US010470946B2

(12) United States Patent
Miyama et al.

(10) Patent No.: US 10,470,946 B2
(45) Date of Patent: Nov. 12, 2019

(54) ABSORBENT ARTICLE

(71) Applicant: UNICHARM CORPORATION, Shikokuchuo-shi, Ehime (JP)

(72) Inventors: Takuya Miyama, Kanonji (JP); Satoru Sakaguchi, Kanonji (JP); Masashi Uda, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 16/300,581

(22) PCT Filed: May 25, 2016

(86) PCT No.: PCT/JP2016/065517
§ 371 (c)(1),
(2) Date: Nov. 12, 2018

(87) PCT Pub. No.: WO2017/195384
PCT Pub. Date: Nov. 16, 2017

(65) Prior Publication Data
US 2019/0240085 A1 Aug. 8, 2019

(30) Foreign Application Priority Data
May 13, 2016 (JP) .................................. 2016-096718

(51) Int. Cl.
*A61F 13/15* (2006.01)
*A61F 13/20* (2006.01)
(Continued)

(52) U.S. Cl.
CPC .. *A61F 13/51104* (2013.01); *A61F 13/49007* (2013.01); *A61F 13/512* (2013.01); *A61F 13/15203* (2013.01); *A61F 2013/5127* (2013.01)

(58) Field of Classification Search
CPC .......... A61F 13/51104; A61F 13/49007; A61F 13/512; A61F 13/15203; A61F 2013/5127; A61F 13/51108
See application file for complete search history.

(56) References Cited

U.S. PATENT DOCUMENTS 5,268,213 A * 12/1993 Murakami .......... A61F 13/5126
428/163
6,436,081 B1 * 8/2002 Wada .................. A61F 13/4752
604/385.01
(Continued)

FOREIGN PATENT DOCUMENTS

CN 203841923 U 9/2014
JP H11-318976 A 11/1999
(Continued)

OTHER PUBLICATIONS

International Search Report in PCT Application No. PCT/JP2016/065517, dated Aug. 26, 2016, 4pp.
(Continued)

*Primary Examiner* — Michele M Kidwell
(74) *Attorney, Agent, or Firm* — Hauptman Ham, LLP

(57) ABSTRACT

A top sheet of a disposable diaper includes projections and depressions. The projection and the depression extend in the front-back direction, and are arranged alternately in the width direction. The top sheet includes a first region disposed at least in the rear waistline region and a second region disposed at least in a crotch region. A height of the first projection is higher than a height of the second projection. A first depression is provided with a widthwise projection configured to divide a space in a first depression extending in a front-back direction. A pitch of the first projection in the width direction is larger than a pitch of the second projection in the width direction.

11 Claims, 12 Drawing Sheets

(51) Int. Cl.
*A61F 13/511* (2006.01)
*A61F 13/49* (2006.01)
*A61F 13/512* (2006.01)

(56) References Cited

U.S. PATENT DOCUMENTS

| | | | | |
|---|---|---|---|---|
| 6,586,076 | B1* | 7/2003 | Mizutani | A61F 13/511 |
| | | | | 428/156 |
| 6,803,334 | B2* | 10/2004 | Mizutani | A61F 13/512 |
| | | | | 428/103 |
| 7,518,032 | B2* | 4/2009 | Seyler | A61F 13/53713 |
| | | | | 604/383 |
| 7,812,213 | B2* | 10/2010 | Doverbo | A61F 13/15699 |
| | | | | 604/358 |
| 8,784,972 | B2* | 7/2014 | Sato | B32B 3/266 |
| | | | | 428/166 |
| 9,445,951 | B2* | 9/2016 | Moberg-Alehammar | |
| | | | | A61F 13/495 |
| 9,480,609 | B2* | 11/2016 | Kirby | A61F 13/5126 |
| 2001/0014796 | A1* | 8/2001 | Mizutani | A61F 13/512 |
| | | | | 604/367 |
| 2002/0013567 | A1* | 1/2002 | Mishima | A61F 13/4946 |
| | | | | 604/385.101 |
| 2002/0028624 | A1* | 3/2002 | Mizutani | A61F 13/512 |
| | | | | 442/394 |
| 2017/0014281 | A1 | 1/2017 | Xie et al. | |

FOREIGN PATENT DOCUMENTS

| | | |
|---|---|---|
| JP | 2009-89965 A | 4/2009 |
| JP | 2009-101091 A | 5/2009 |
| JP | 2009-136349 A | 6/2009 |
| JP | 4990070 B2 | 8/2012 |
| JP | 2013-147784 A | 8/2013 |

OTHER PUBLICATIONS

Office Action in CN Application No. 201680085503.0, dated May 29, 2019, 10pp.

* cited by examiner

ABSORBENT ARTICLE

RELATED APPLICATIONS

The present application is a National Phase of PCT/JP2016/065517, filed May 25, 2016, and claims priority based on Japanese Patent Application No. 2016-096718, filed May 13, 2016.

TECHNICAL FIELD

The present invention relates to an absorbent article configured to absorb urine and feces.

BACKGROUND ART

As one of absorbent articles for absorbing urine and feces of wearers in the related art, an absorbent article having a top sheet with different configurations depending on regions such as a region for absorbing urine and a region for absorbing feces have been provided (see Patent Literature 1, for example).

The absorbent articles of Patent Literature 1 include a skin contact sheet that comes into contact with a wearer. A feces passage opening configured to allow passage of feces is formed in a skin contact sheet that comes around a rear waistline region, and a plurality of excremental liquid inflow holes are formed in a skin contact sheet that comes around a front waistline region.

CITATION LIST

Patent Literature

Patent Literature 1: U.S. Pat. No. 4,990,070

SUMMARY OF INVENTION

A feces passage opening of the absorbent article of Patent Literature 1 penetrates through the skin contact sheet. Feces passed through the feces passage opening is stored in a space provided on a non-skin-facing side of the feces passage opening. The feces stored in the space may reattached to the wearer's skin when the skin of the wearer touches, and may come out of the space.

The excremental liquid inflow holes in the front waistline region are intermittently arranged in a plane direction, and thus body fluids cannot be diffused in the plane direction. Consequently, urine may not always be quickly absorbed.

Accordingly, it is an object of the present invention to provide an absorbent article capable of absorbing urine and feces exhibiting different behaviors adequately by absorbing urine quickly and retaining the feces once stored continuously.

An absorbent article (disposable diaper 10) according to the present invention includes: a front waistline region (front waistline region 20), a rear waistline region; a crotch region (crotch region 25) located between the front waistline region and the rear waistline region (rear waistline region 30);

a front-back direction (front-back direction L) from the front waistline region toward the rear waistline region, a width direction orthogonal to the front-back direction (width direction W);

an absorber (absorber 40) extending across the crotch region and extending to at least one of the front waistline region and the rear waistline region; and a top sheet (top sheet 50) located on a skin-facing side with respect to the absorber and coming into contact with a wearer, the top sheet including projections (projections 51) projecting toward a skin-facing side and depressions (depressions 52) provided between the projections, the projections and the depressions extending in the front-back direction and being arranged alternately in the width direction, wherein the top sheet includes a first region (first region R1) disposed at least in the rear waistline region and a second region (second region R2) disposed at least in the crotch region, a height of the projections (first projections 511) in the first region is larger than a height of the projections (second projections 512) in the second region, each of the depressions in the first region includes a dividing portion (widthwise projections 57) configured to divide a space in each of the depressions, the space extending in the front-back direction, and a pitch of the projections in the first region in the width direction is larger than a pitch of the projections in the second region in the width direction.

BRIEF DESCRIPTION OF DRAWINGS

FIG. 7A illustrates a moving state in the first region, and FIG. 7B illustrates a moving state in the second region.

DESCRIPTION OF EMBODIMENT

Figure 1:
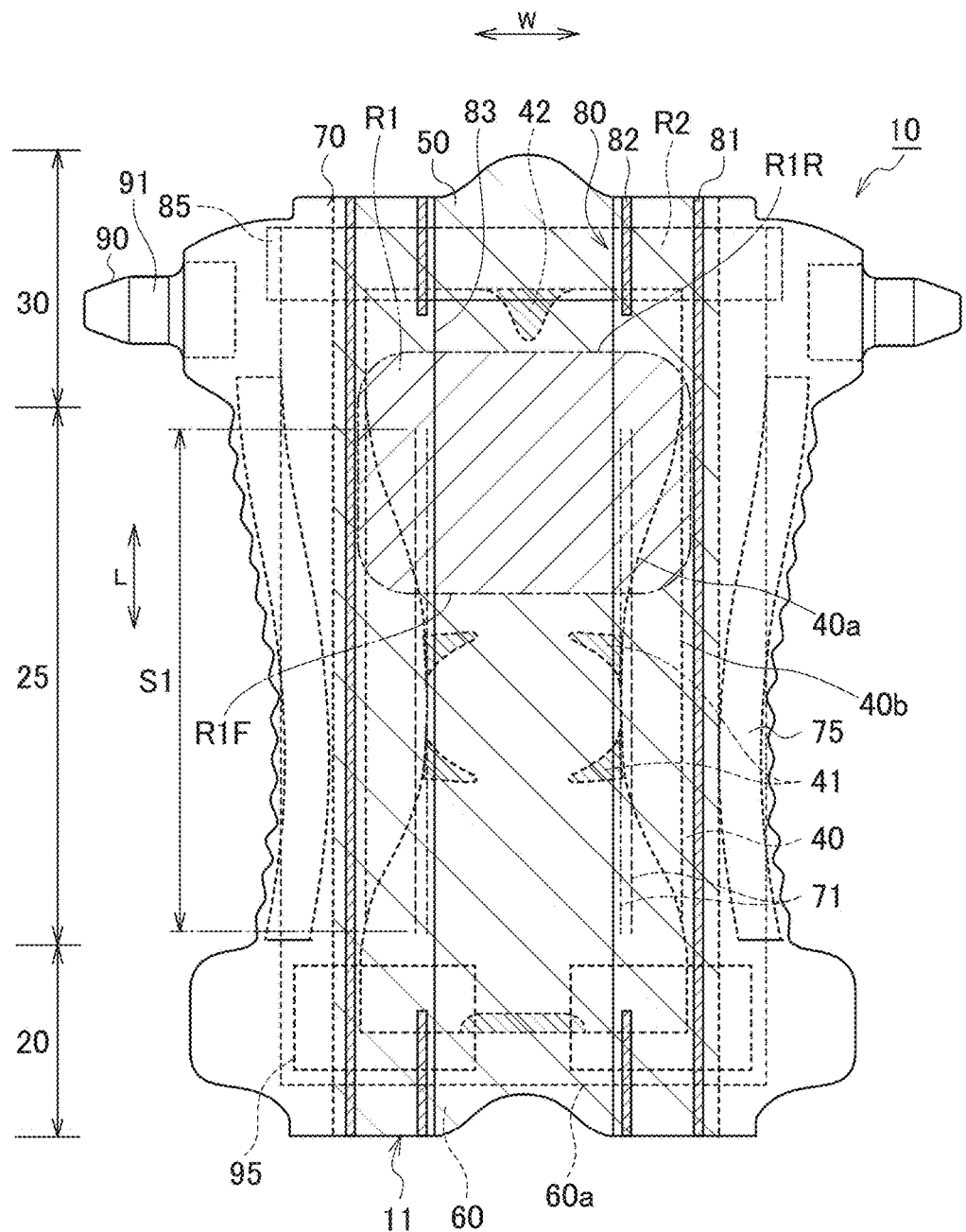
FIG. 1 is a deployed plan view of a disposable diaper according to the present exemplary embodiment.

From this specification and description in conjunction with the attached drawings, at least the following respects become apparent.

An absorbent article including:

a front waistline region; a rear waistline region; a crotch region located between the front waistline region and the rear waistline region;

a front-back direction from the front waistline region toward the rear waistline region; a width direction orthogonal to the front-back direction;

an absorber extending across the crotch region and extending to at least one of the front waistline region and the rear waistline region; and a top sheet located on a skin-facing side with respect to the absorber and coming into contact with a wearer, the top sheet including projections projecting toward a skin-facing side and depressions provided between the projections, the projections and the depressions extending in the front-back direction and being arranged alternately in the width direction, wherein the top sheet includes a first region disposed at least in the rear waistline region and a second region disposed at least in the crotch region, a height of the projections in the first region is larger than a height of the projections in the second region, each of the depressions in the first region includes a dividing portion configured to divide a space in each of the depressions, the space extending in the front-back direction, and a pitch of the projections in the first region in the width direction is larger than a pitch of the projections in the second region in the width direction.

According to the absorbent article as described above, urine may be absorbed quickly and feces exhibiting different behaviors adequately by absorbing urine quickly and retaining the feces once stored continuously may be provided. The second region includes a region disposed at least in the crotch region for receiving discharged urine. The first region includes a region disposed at least in the rear waistline region for receiving discharged feces. The shapes of the projections and the depressions in the first region are different from the shapes of the projections and depressions in the second region, and thus the user can figure out a difference between an absorbing performance of the top sheet disposed in the crotch region and an absorbing performance of the top sheet disposed in the rear waistline region, and thus may feel assured that both of urine and feces are adequately absorbed.

When feces are discharged on the first region, the feces are stored in the depressions between the projections. At this time, since the height of the projections in the first region is higher than the height of the projections in the second region, relatively high walls may be formed for holding feces. Since the walls of the projections that hold feces are high, feces stored once in the depressions may easily be retained by holding by the walls. Consequently, even when the wearer's skin touches the surface of feces stored in the depressions, the feces is continuously retained in the depressions and is prevented from exiting the depressions and re-attaching to the wearer.

Since the pitch of the projections in the first region in the width direction is longer than the pitch of the projections in the second region in the width direction, spaces between the projections in the first region become wider and thus spaces for storing feces may be widely formed. Therefore, feces discharged on the top sheet are stored in the depressions and thus can hardly remain on the projections. Contact of feces with the wearer's skin is prevented or reduced, and thus wear feeling is improved. In addition, more feces can be retained in the depressions of the first region, and thus the own weight of feces in the depressions is increased. With the increase in own weight of feces, the top sheet having fibers allows moisture contained in the feces to pass through gaps between the fibers into the absorber. Therefore, the moisture in the feces is transferred quickly into the absorber, and thus loose feces containing much moisture is prevented or reduced from being continuously in kept in contact with the skin.

The dividing portion configured to divide a space in each of the depressions extending in the front-back direction is provided in each of the depressions in the first region. Therefore, feces stored in the depressions are prevented from being diffused in the front-back direction. In the second region, urine can be diffused by the projections and the depressions in the front-back direction, and thus the urine can be transferred to the absorber quickly and stored. By continuously holding the feces in the first region, attachment of body fluids and feces to the wearer's skin is prevented or reduced, and thus an improvement of wear feeling is achieved. With the first region and the second region of the top sheet, urine and feces having different features can be absorbed adequately.

In the absorbent article as described above, the depressions in the second region are preferably disposed continuously from a front end edge of the first region to a front end edge of the top sheet.

According to the absorbent article as described above, since the depressions in the second region are formed continuously, body fluids may be diffused from the front end edge of the first region to the front end edge of the top sheet to quickly transfer urine to the absorber in a large surface area. Accordingly, urine may be absorbed further quickly.

In the absorbent article as described above, each of the projections preferably include a projecting wall portion extending from an outer edge of the projection toward the skin-facing side, each of the depressions include a depressed bottom portion extending in the front-back direction and the width direction, and an angle formed between the projecting wall portion and the depressed bottom portion of the depression adjacent to the projecting wall portion in the first region is larger than an angle formed between the projecting wall portion and the depressed bottom portion of the depression adjacent to the projecting wall portion in the second region.

According to the absorbent article as described above, a rising angle of the projecting wall portion in the first region is larger than a rising angle of the projecting wall portion in the second region, and thus the projecting wall portion in the first region is a relatively steep inclination. Therefore, excrement stored in the depressions may be held from both sides to retain the feces in the first region, and thus excrement once stored is prevented from exiting the depressions.

The rising angle of the projecting wall portion in the second region is smaller than the rising angle of the projecting wall portion in the first region, and the projecting wall portion in the second region has a relatively gentle inclination. The second region is disposed at least in the crotch region. The crotch region is in tight contact with the wearer's skin compared with the rear waistline region. Since the projecting wall portion of the second region has a gentle inclination, contact of projections with the skin may be alleviated even when the crotch region located in the second region is in tight contact with the skin.

In the absorbent article described above, the top sheet includes fibers, a space is formed between the projections and the absorber, the fibers in the projecting wall portion preferably includes fibers oriented along a thickness direction of the top sheet more than fibers oriented along the front-back direction and the width direction.

According to the absorbent article configured as described above, since spaces are formed on the non-skin-facing side of the projections, contact of the projections with respect to the skin becomes soft and thus the wearer can have a fluff feeling. The fibers of the projecting wall portions include many fibers oriented in the thickness direction, and thus body fluids tend to be introduced in the thickness direction. Therefore, even when the height of the projections is high, body fluids in the projecting wall portions may be introduced quickly toward the absorber, and thus remaining of the body fluids in the projecting wall portions are prevented or reduced.

In the absorbent article described above, a pair of three-dimensional gathers disposed on both outer sides in the width direction of a widthwise center of the absorbent article is provided, each of the three-dimensional gathers includes an erectile portion including a resilient member elastic in the front-back direction and capable of erecting toward the wearer, and the projections and the erectile portion are disposed across the first region and the second region.

According to the absorbent article as described above, since the projections are disposed across the first region and the second region, no difference in rigidity created by discontinuity of the projection is formed in a boundary between the first region and the second region. Therefore, a bending point created by the difference in rigidity at the discontinuity of the projections can hardly be formed in a region having the erectile portion erecting (rising) and the erectile property of the three-dimensional gather may be maintained. In addition, leakage prevention walls formed by the three-dimensional gathers are provided to cover outer sides in the width direction of feces stored in the depressions, and thus attachment of feces to portions around the wearer's legs may be prevented. In addition, by introducing urine along the projections in the front-back direction, the urine can be diffused across the first region and the second region and urines are transferred further quickly to the absorber.

In the absorbent article as described above, each of the depressions in the first region preferably includes a depressed bottom portion extending in the front-back direction and the width direction and an intermediate portion projecting toward the skin-facing side with respect to the depressed bottom portion, and a top portion of the intermediate portion is located on a non-skin-facing side of top portions of the projections in the first region.

With the absorbent article as described above, the intermediate portions are provided in the depressions in the first region. Therefore, when the projections in the first region are deformed in the falling direction, the projections in the first region are caught by the intermediate portions, and thus the depressions in the first region are prevented from being completely covered by the projections in the first region. The top portions of the intermediate portions are located on the non-skin-facing side with respect to the top portions of the projections and the height of the intermediate portions is low. Therefore, when the intermediate portions and the projections are deformed in a falling direction, the depression can hardly be covered with the intermediate portions and the projections. Therefore, when feces are discharged, the feces can be maintained in a state of being easily introduced into the depressions.

In the absorbent articles described above, preferably, the top sheet includes fibers, each of the depressions includes a depressed bottom portion extending in the front-back direction and the width direction and a groove portion depressed toward the non-skin-facing side with respect to the depressed bottom portion, the groove portion includes a groove wall portion extending from the depressed bottom portion toward the non-skin-facing side and a groove bottom portion located on the non-skin-facing side with respect to the groove wall portion, and in the first region, a density of the fibers of the groove wall portion is lower than a density of fibers in the groove bottom portion.

With the absorbent article in this configuration, since the density of the fibers of the groove wall portions in the first region is relatively low, moisture contained in excrement such as feces stored in the depressions in the first region may be introduced into the absorber via voids between fibers. In addition, since the density of the fibers in the groove bottom portions in the first region is relatively high, fibers of the groove wall portions can be continuously in contact with feces stored in the depressions in the first region, and thus the feces can easily be retained by being surrounded by the groove wall portions and the groove bottom portions. Therefore, feces are prevented from exiting the depressions in the first region and reattaching to the wearer.

In the absorbent article described above, preferably, a pair of three-dimensional gathers are disposed on both of the outer sides in the width direction of the widthwise center of the absorbent article, and each of the three-dimensional gather includes: the erectile portion including a resilient member elastic in the front-back direction and configured to be capable of erecting toward the wearer, and a first fixed portion located outside the erectile portion in the width direction and serves as a starting point of an erecting movement of the erectile portion, and the first region is disposed between a pair of the first fixed portions in the width direction.

According to the absorbent article as described above, rigidity of the top sheet between the first fixed portions in the rear waistline region is enhanced and thus the height of the erectile portions may be easily created. Therefore, sideward leakage of feces in the rear waistline region may be prevented. In addition, since the erectile portions can easily erect, the top sheet is prevented from being covered with the three-dimensional gathers, and thus discharged feces can be introduced into the depressions in the first region.

In the absorbent article as described above, preferably, the three-dimensional gathers are located at both outer sides of the erectile portion in the front-back direction and each include a second fixed portion, the second fixed portion serves as a starting point of an erecting motion of the erectile portion, and a rear end edge of the first region is located rearward of a region of the erectile portion contracted by the resilient member.

The second fixed portion side of the erectile portion is closer to the rising point, and thus the rising height can hardly be created compared with the center of the erectile portion in the front-back direction. Also, a region rearward of the contracting region is not contracted by the resilient member, and thus the rising height of the erectile portion can hardly be created. Since the first region is disposed rearward of the contracting region, rigidity of the top sheet on the second fixed portion side in the rear waistline region is increased, and thus the height of the erectile portion is easily created. Therefore, sideward leakage of feces in the rear waistline region may be prevented. In addition, since the erectile portions can easily rise, the top sheet is prevented from being covered with the three-dimensional gathers, and thus discharged feces can be introduced into the depressions in the first region.

In the absorbent article described above, preferably, a pair of fastening tapes is provided in the rear waistline region, the pair of fastening tapes extending outward in the width direction, the fastening tape includes a fastening portion to be fastened to the front waistline region, and the first region is at a distance from a region between the pair of fastening portions.

The region between the pair of fastening portions is an area where the fastening portions come into tight contact with the body in a state of being fastened to the front waistline region. Since the region between the pair of fastening portions and the first region are apart from each other, a state in which feces stored in the depressions in the first region is separated from the wearer's skin is easily achieved.

In the absorbent article described above, preferably, a waist elastic portion is disposed in the rear waistline region and elastic in the width direction, and the first region is at a distance from an area where the waist elastic portion is disposed.

The region where the waist elastic portion is disposed is a region coming into tight contact with the body in a worn state. Since the first region and the region where the waist elastic portion is disposed are at the distance from each other, a state in which feces stored in the depressions in the first region is separated from the wearer's skin is easily achieved.

In the absorbent article described above, preferably, the dividing portion projects toward the skin-facing side with respect to the depressed bottom portion, the depressed bottom portion extending in each of the depressions in the first region in the front-back direction and the width direction, and the dividing portion is disposed along the width direction between the projections in the first region, the top portions of the projections in the first region is located on the skin-facing side with respect to a top portion of the dividing portion.

According to the absorbent article described above, since the dividing portions extending in the width direction are provided in the first regions, feces stored in the depressions by the dividing portions is prevented from being diffused in the front-back direction.

In addition, since the top portions of the projections in the first region are located on the skin-facing side with respect to the top portions of the dividing portions, excrement in the depressions is easily diffused along the front-back direction and can hardly be diffused along the width direction. Therefore, feces are prevented from leaking sideward.

Disposable Diaper According to the Present Exemplary Embodiment

Referring now to the drawings, an exemplary embodiment of a disposable diaper 10 as an absorbent article of the present invention will be described. Note that the absorbent article of the present invention is not limited to the disposable diapers and also includes absorbent pads to be attached to undergarments or diapers. In the description of the drawings given below, the same or similar parts are designated by the same or similar reference symbols. However, it should be noted that the drawings are schematic illustrations and the ratios of respective dimensions are different from actual ratios. Therefore, specific dimensions should be calculated by taking the following description into account. Among the drawings, parts having different dimensional relationships or ratios may be included.

(1) General Configurations of Disposable Diaper

FIG. 1 is a deployed plan view of a disposable diaper 10 according to the present exemplary embodiment. The deployed plan view in FIG. 1 illustrates an expanded state in which elastic portions such as a three-dimensional gather and a waist elastic portion is expanded until wrinkles of a top sheet 50 and side sheets 70 constituting the disposable diaper are no longer formed.

The disposable diaper 10 includes a front waistline region 20, a crotch region 25, and a rear waistline region 30. The front waistline region 20 is a portion coming into contact with a front waistline region (belly portion) of a wearer. The rear waistline region 30 is a portion coming into contact with the rear waistline region (back portion) of the wearer. The crotch region 25 is located between the front waistline region 20 and the rear waistline region 30. In the present exemplary embodiment, a direction from the front waistline region 20 toward the rear waistline region 30 is referred to as a front-back direction L, a direction orthogonal to the front-back direction L is referred to as a width direction W, and a direction extending between a skin-facing side T1 and a non-skin-facing side T2 of the wearer is referred to as a thickness direction T.

The disposable diaper 10 includes an absorber 40. The absorber 40 lies across the crotch region 25, and extends toward at least one of the front waistline region 20 and the rear waistline region 30. The absorber 40 of the present exemplary embodiment is disposed across the front waistline region 20, the crotch region 25, and the rear waistline region 30. The absorber 40 includes an absorbing core 40a and a core wrap 40b.

In the crotch region 25 of the absorber 40, first low basis-weight portions 41 extending inward from outer edges (outer ends in the width direction) of the absorbing core 40a in the width direction W is formed. The first low basis-weight portions 41 are disposed respectively at both of the outer edges of the absorbing core 40a and are disposed at a distance in the front-back direction L. The rear waistline region 30 of the absorbing core 40a is provided with a second low-basis-weight portion 42 extending forward from a rear end edge of the absorbing core 40a. A length of the second low-basis-weight portions 42 in the width direction is reduced gradually toward the front. The first low basis-weight portions 41 and the second low-basis-weight portion 42 are portions being low in basis weight of the absorbing material compared with the absorbing core in the periphery. The first low basis-weight portions 41 and the second low-basis-weight portion 42 in the present exemplary embodiment are cutouts.

A liquid-permeable top sheet 50 is provided on the skin-facing side of the absorber 40. The top sheet 50 constitutes a skin-contact surface of the disposable diaper 10 and thus comes into contact with the wearer. The top sheet 50 is disposed across the front waistline region 20, the crotch region 25, and the rear waistline region 30. The top sheet 50 has fibers, and specifically, may be formed of a non-woven fabric. The top sheet 50 will be described later in detail.

The absorber 40 is provided with a liquid-impermeable back sheet (not illustrated) on the non-skin-facing side. The non-skin-facing side of the back sheet is provided with an outer sheet (not illustrated).

A pair of three-dimensional gathers 80 are disposed on both widthwise outer sides of a widthwise center of the disposable diaper 10. The three-dimensional gathers 80 are erectile gathers capable of rising toward the wearer. The three-dimensional gathers 80 are each composed of the side sheet 70 and a side resilient member 71 as a resilient member.

The side resilient members 71 configured to expand and contract in the front-back direction are disposed on inner edge sides of the side sheets 70. The pair of three-dimensional gathers 80 are substantially line symmetry with respect to an axis of symmetry extending along the widthwise center of the disposable diaper. The three-dimensional gathers 80 each include a side resilient member 71 expanding and contracting in the front-back direction, and include an erectile portion 83 capable of rising toward the wearer, a first fixed portion 81 located outside the erectile portion 83 in the width direction and serves as a starting point of erection (rising) of the erectile portion 83, and a second fixed portion 82 located on an outer side of the erectile portion 83 in the front-back direction L and serves as a starting point of rising of the erectile portion 83. A front end edge of the erectile portion 83 matches a rear end edge of the second fixed portion 82 disposed in the front waistline region, and a rear end edge of the erectile portion 83 matches a front end edge of the first fixed portion 81 disposed in the rear waistline region.

The side sheets 70 cover outer edges of the top sheet. The side sheets 70 are joined onto the top sheet 50 at the first fixed portions 81 and the second fixed portions 82. The erectile portions 83 are provided between the second fixed portions 82 in the front-back direction L without being joined to the top sheet 50, and thus are capable of rising from the top sheet 50. The erectile portions 83 erect toward the wearer in a state in which the side resilient members are contracted. The erectile portions 83 erect toward the wearer in a state in which the disposable diaper is worn. The erectile portions 83 each include a contracting region S1 in which the side resilient member 71 is disposed in the contractible manner. The contracting region S1 is a region where the side resilient member 71 is joined in a state of being expanded in an expanded state in which the disposable diaper is expanded. The contracting region S1 is conceptually a region excluding regions of the erectile portions 83 in which the side resilient members 71 are not provided, excluding regions in which the side resilient members 71 in the non-expanded state are joined, and excluding regions of the side resilient members 71 not joined to the side sheets 70. The three-dimensional gathers 80 form walls rising toward the skin-facing side along outer edges of the absorber 40 to prevent excrement from leaking sideward.

On the outer edges of the disposable diaper 10, leg openings 13 to be placed around the legs of the wearer is formed. The disposable diaper 10 is provided with a pair of leg elastic portion 75 placed inside the leg openings 13 in the width direction and being capable of expanding and contracting in the front-back direction L. The leg elastic portions 75 are disposed inside the left and right leg openings 13 in the width direction.

A pair of fastening tapes 90 extend outward of the side sheets 70 in the width direction W in the rear waistline region 30. Fastening tapes 90 each have a fastening portion 91 to be fastened to a target portion 95 in the front waistline region 20. The fastening portion 91 is provided with, for example, an engagement hook. The fastening tapes 90 serve to hold the disposable diaper 10 to the wearer's body by being fastened to target portions 95 in the front waistline region 20. The fastening tapes 90 are attached respectively to the side sheets 70.

The target portions 95 are provided on a surface of the outer sheet of the front waistline region 20 on the non-skin-facing side. The target portions 95 are configured to catch the engagement hooks of the fastening tapes 90, and function as loops of a hook-and-loop engagement system.

The disposable diaper 10 includes a waist elastic portion 85 capable of expanding and contracting in the width direction. The waist elastic portion 85 is disposed in the rear waistline region 30. The waist elastic portion 85 is disposed between the pair of fastening tapes 90 and contracts a portion between the fastening tapes 90 in the width direction. The waist elastic portion 85 is disposed to overlap at least partly with the second low-basis-weight portion 42 of the absorber. The waist elastic portion 85 of the present exemplary embodiment is disposed in a region overlapping with a rear end edge of the second low-basis-weight portion 42 and is disposed in a region not overlapping with a front end edge of the second low-basis-weight portion 42.

(2) Configuration of Top Sheet

Figure 2:
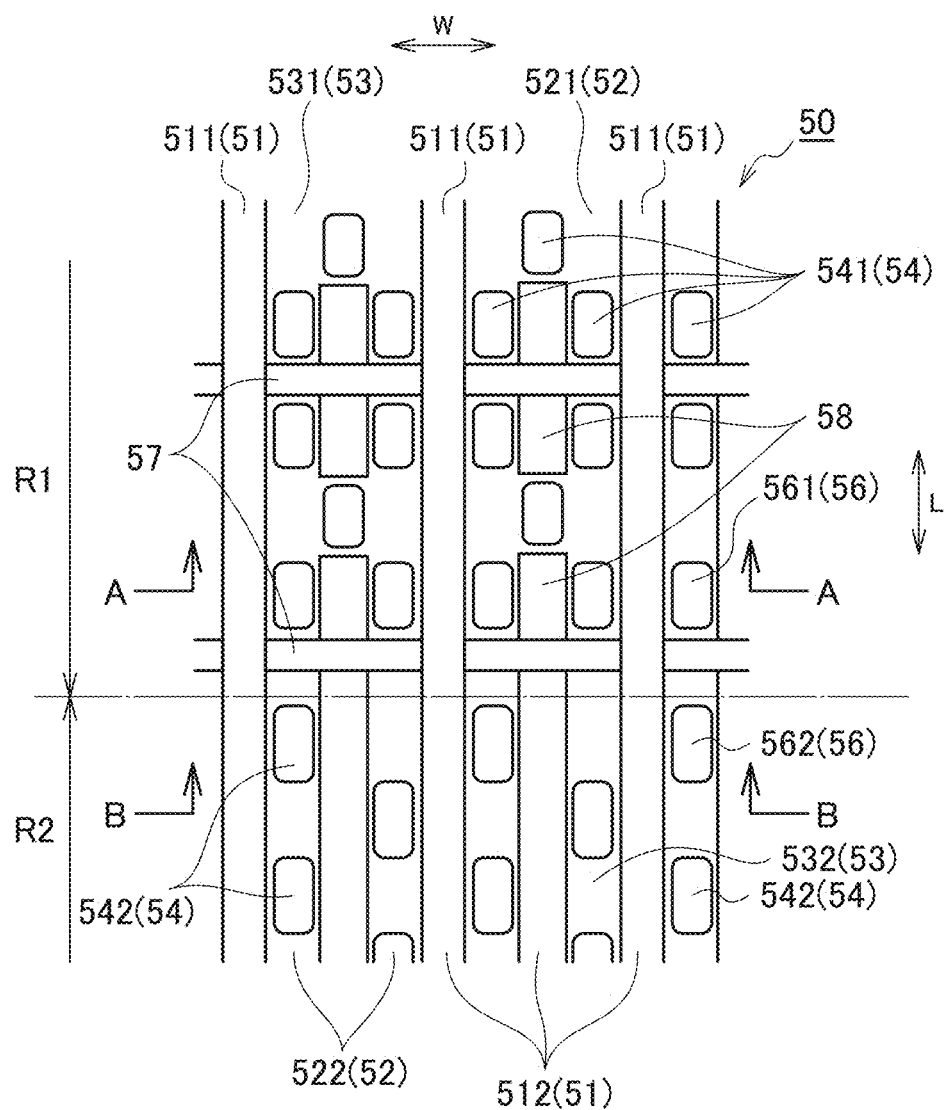
FIG. 2 is a partly enlarged plan view of a top sheet of the disposable diaper illustrated in FIG. 1.

Detailed description of the configuration of the top sheet 50 will be given below. FIG. 2 is an enlarged plan view of the top sheet. The top sheet 50 includes projections 51 projecting on the skin-facing side and depressions 52 depressed on the non-skin-facing side T2 with respect to the projections 51. In the plan view illustrated in FIG. 1, the projections 51 and the depressions 52 are omitted. The projections 51 project on the skin-facing side of the disposable diaper 10, and the depressions 52 are spaces depressed on the non-skin-facing side with respect to top portions of the projections. The projections 51 and the depressions 52 extend in the front-back direction L, and are arranged alternately in the width direction W. The projections 51 and the depressions 52 are formed over the entire surface of the top sheet 50. Note that the projections 51 and the depressions 52 may be formed only over part of the top sheet 50. The projections 51 have projection wall portions 59 extending in the thickness direction. The projecting wall portions 59 each extend from the top of the projection 51 and the depressed bottom portion 53 of the depression 52.

As used in the present exemplary embodiment the term "extends in the front-back direction" needs at least to be a configuration having a certain range in the front-back direction and also includes a configuration extending in the width direction while inclining with respect to the front-back direction at an angle smaller than 45 degrees with respect to the front-back direction. As used herein the term "extends in the width direction" needs at least to be a configuration having a certain range in the width direction and also includes a configuration extending in the front-back direction while inclining with respect to the width direction at an angle smaller than 45 degrees with respect to the width direction.

Figure 3:
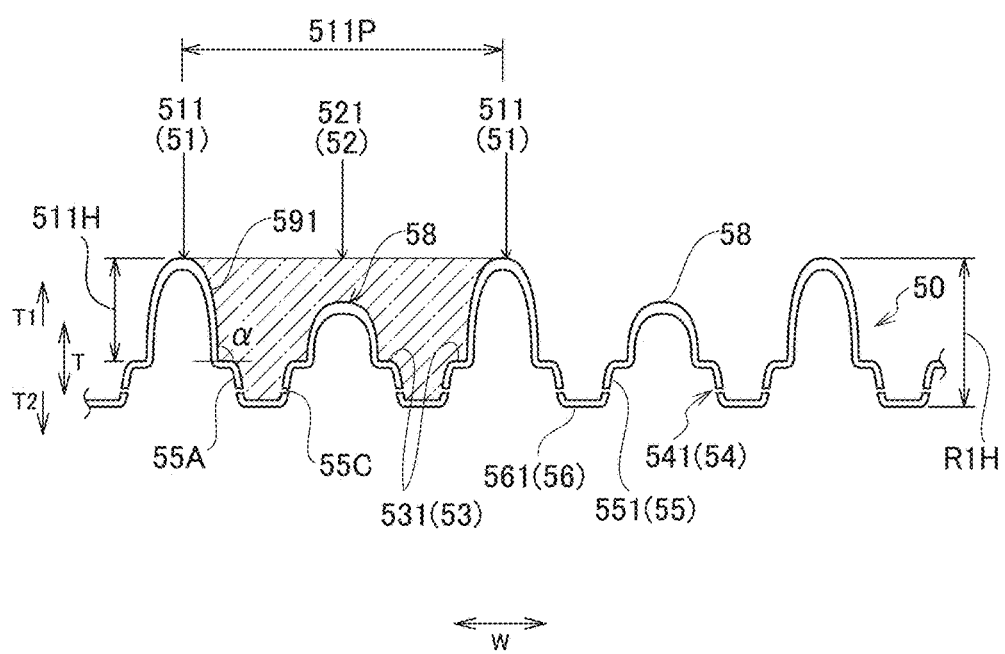
FIG. 3 is a cross-sectional view taken along line A-A in FIG. 2.
Figure 5:
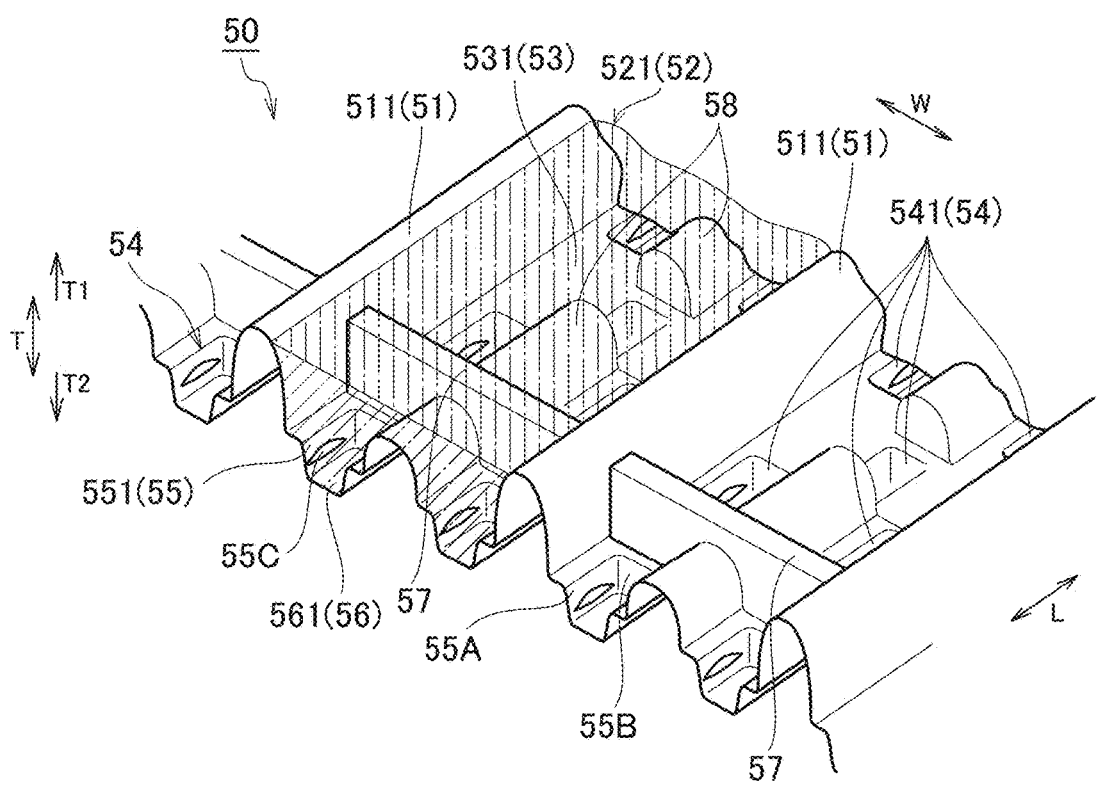
FIG. 5 is a partly broken perspective view schematically illustrating a first region of the top sheet.

The depressions 52 are spaces interposed between the projections in the width direction. More specifically, each of the depressions is a space surrounded by projecting wall portions facing each other in the width direction, the depressed bottom portion, and a groove portion. A surface of each of the depressions on the non-skin-facing side corresponds to a groove bottom portion of the groove portion, and a surface of each of the depression on the skin-facing side corresponds to an imaginary surface connecting top portions of the projecting wall portions disposed face to face in the width direction. In FIG. 3 and FIG. 5, a region of the depression is indicated by hatching.

The depression 52 includes a depressed bottom portion 53 extending in a plane direction including the front-back direction L and the width direction W, and groove portions 54 depressed toward the non-skin-facing side T2 with respect to the depressed bottom portion 53. The groove portions 54 have a substantially rectangular shape in plan view. The groove portions 54 are provided in the depression 52 discontinuously in the front-back direction L, and are formed at a distance in the front-back direction L and the width direction W. The groove portions 54 each includes groove wall portions 55 extending from the depressed bottom portion 53 to the non-skin-facing side T2, a groove bottom portion 56 located on the non-skin-facing side T2 with respect to the groove wall portions 55 and extending in the plane direction, widthwise projections 57 as dividing portions, and an intermediate portion 58. The groove wall portion 55 includes first groove surfaces 55A located at outer edges of the groove portion 54 and extending in the front-back direction L, and second groove surfaces 55B located at end edges of the groove portion 54 in the front-back direction L and extending in the width direction W. In the first groove surface 55A, a hole 55C penetrating therethrough is formed. The hole 55C is positioned on the groove bottom portion 56 side with respect to a center of the groove wall portion 55 in the thickness direction.

The top sheet 50 includes a first region R1 and a second region R2. In FIG. 1, the first region R1 and the second region R2 are indicated with hatching different from each other.

The first region R1 is disposed at least in the rear waistline region 30. Therefore, mainly feces are discharged on the first region R1. When feces are discharged on the first region R1, the feces is stored in the depressions 52 between the projections 51. The second region R2 is disposed in the crotch region 25 at least forward of the first region R1. Therefore, mainly urine is discharged on the second region R2. When urine is discharged on the first region R1, urine is diffused along the depressions 52 between the projections 51 in the front-back direction L and is guided to the absorber 40. The second region R2 needs only be disposed at least forward of the first region R1, and the second region R2 in the present exemplary embodiment is disposed over the entire region of the top sheet 50 except for the first region R1, and thus the first region R1 is surrounded by the second region R2 in plan view.

Figure 4:
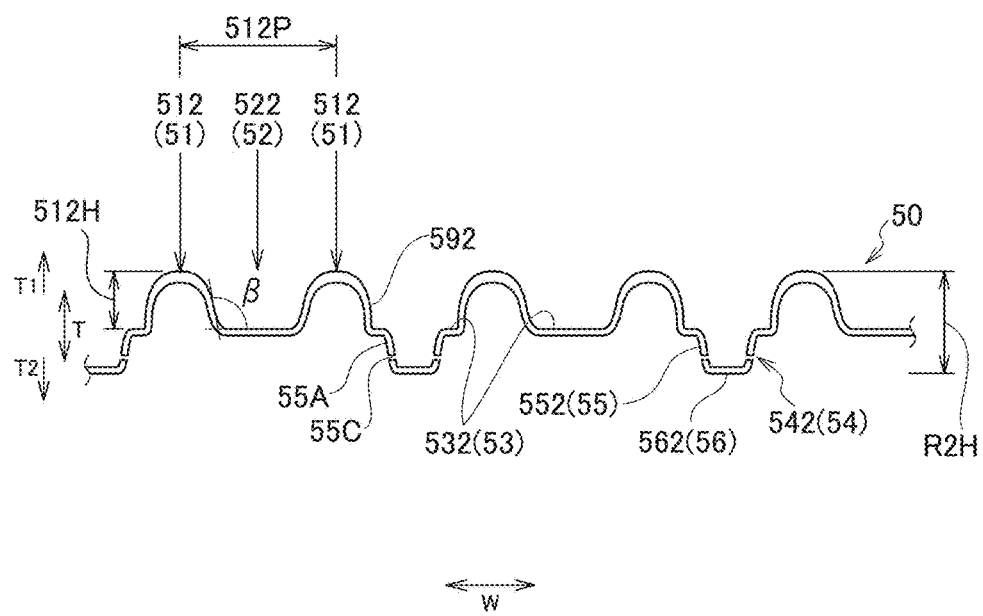
FIG. 4 is a cross-sectional view taken along line B-B in FIG. 2.
Figure 6:
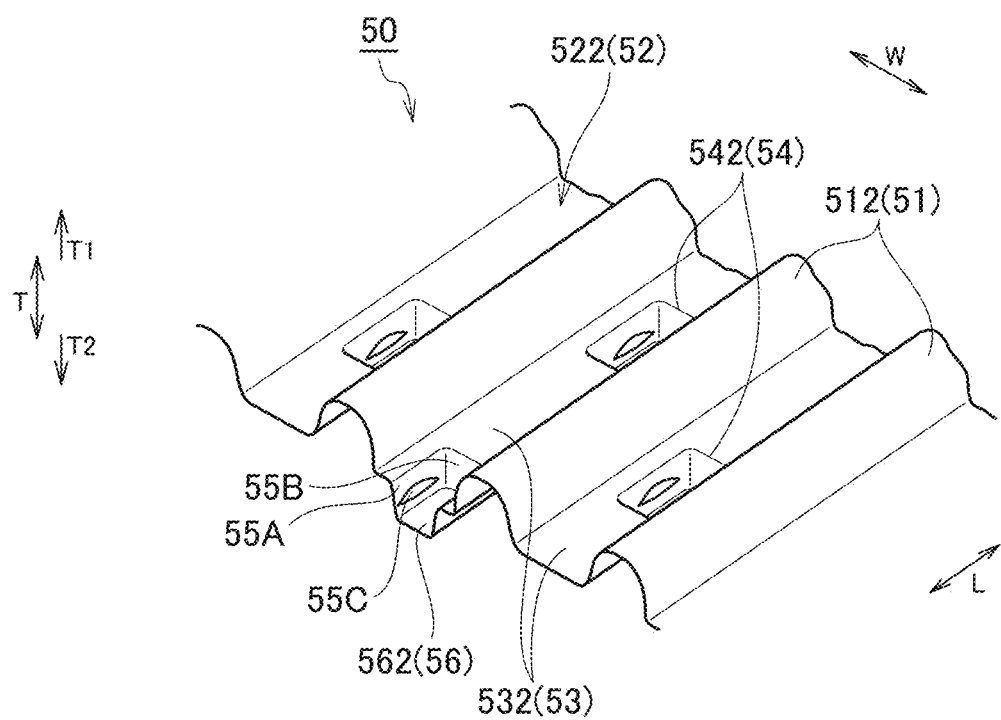
FIG. 6 is a partly broken perspective view schematically illustrating a second region of the top sheet.

The shape of the top sheet 50 in the first region R1 is different from the shape of the top sheet 50 in the second region R2. FIG. 3 and FIG. 5 are drawings schematically illustrating the top sheet 50 in the first region R1. FIG. 4 and FIG. 6 are drawings schematically illustrating the top sheet 50 in the second region R2. The shapes of the projections and the depressions in the first region R1 are different from the shapes of the projections and depressions in the second region R2, and thus the user can figure out a difference between an absorbing performance of the top sheet 50 disposed in the crotch region 25 and an absorbing performance of the top sheet 50 disposed in the rear waistline region 30, and thus may feel assured that both of urine and feces are adequately absorbed.

The projection 51 includes a first projection 511, which is a projection in the first region R1, and a second projection 512, which is a projection in the second region R2. The depression 52 includes a first depression 521, which is a depression in the first region R1, and a second depression 522, which is a depression in the second region R2. The depressed bottom portion 53 includes a first depressed bottom portion 531, which is a depressed bottom portion in the first region R1, and a second depressed bottom portion 532, which is a depressed bottom portion in the second region R2. The depression 52 includes the groove portions 54. The groove portion 54 includes a first groove portion 541, which are groove portions in the first region R1, and second groove portions 542, which are groove portions in the second region R2. The groove wall portion 55 includes a first groove wall portion 551, which are groove wall portions in the first region R1, and second groove wall portions 552, which are groove wall portions in the second region R2. The groove bottom portion 56 includes a first groove bottom portion 561, which are groove bottom portions in the first region R1, and second groove bottom portions 562, which are groove bottom portions in the second region R2.

In the top sheet 50 of the first region R1, first projections 511, first depressions 521, intermediate portions 58, and widthwise projections 57 are formed. In the first region R1, the first projections 511 are formed continuously in the front-back direction L, and arranged in a plurality of rows in predetermined intervals in the width direction W. The plurality of rows of the first projections 511 are disposed in parallel with the adjacent first projections 511. The first depressions 521 are provided between the first projections 511 in the width direction W. The first projections 511 and the first depressions 521 are parallel in the front-back direction, and are arranged alternatively in the width direction. The first depressions 521 each include a first depressed bottom portion 531 as the depressed bottom portion 53, the first groove portions 541 as the groove portions 54, the first groove wall portions 551 as the groove wall portions 55, and the first groove bottom portions 561 as the groove bottom portions 56.

Between the first projections 511 in the width direction, the widthwise projections 57 are provided. The widthwise projections 57 constitutes dividing portions configured to divide spaces extending in the front-back direction in the first depressions. The widthwise projections 57 are disposed along the width direction W, and outer edges of the widthwise projections are in contact with the projecting wall portions. Top portions (the top portion on the skin-facing side T1) of the widthwise projections 57 are located on the non-skin-facing side T2 with respect to the top portion (the top portion on the skin-facing side) of the first projections 511. The widthwise projections 57 project toward the skin-facing side T1 with respect to the first depressed bottom portions 531. The widthwise projections 57 are each provided in the entire region of each of the first depressions 521 in the width direction, and divide at least part of the space in each of the first depressions 521 at least in the front-back direction L. More specifically, the regions of the spaces of the first depressions 521 extending in the front-back direction on the skin-facing side (the regions on the skin-facing side with respect to the widthwise projections) are not divided in the front-back direction and extend continuously in the front-back direction. In contrast, regions of the non-skin-facing side of the spaces of the first depressions 521 extending in the front-back direction (regions where the widthwise projections are disposed) are divided in the front-back direction, and are not continuous in the front-back direction. The widthwise projections 57 are provided at a distance in the front-back direction L. Therefore, the first depressions 521 are not continuous at least partly in the front-back direction L. When feces are discharged on the first region R1, the feces is stored in the first depressions 521 between the first projections 511. Feces stored in the first depressions 521 is prevented or reduced from diffusing in the front-back direction L by portions of the first depressions 521 not continuous in the front-back direction L. Since the top portions of the first projections 511 are located on the skin-facing side T1 with respect to the top portions of the widthwise projections 57, excrement in the first depressions 521 is easily diffused along the front-back direction L and can hardly be diffused along the width direction W. Therefore, feces are prevented from leaking sideward.

The intermediate portions 58 are disposed between the first projections 511 in the width direction and in the first depressions 521. The intermediate portions 58 are provided along the front-back direction. The intermediate portions 58 project toward the skin-facing side T1 with respect to the first depressed bottom portions 531. The top portions of the intermediate portions 58 are located on the non-skin-facing side T2 with respect to the top portions of the first projections 511. The intermediate portions 58 are disposed at a center of the region between the first projections 511 in the width direction. The first depressed bottom portions 531 are disposed respectively outside the intermediate portions 58 in the width direction. The intermediate portions 58 are disposed between the widthwise projections in the front-back direction L. In a region surrounded by a pair of the first projections adjacent to each other in the width direction W and a pair of the widthwise projections 57 adjacent in the front-back direction L, the intermediate portions 58 are disposed at a center of the region in the width direction W, and are disposed separately in the front-back direction. The first depressed bottom portions 531 and the first groove portions 541 are provided between the intermediate portions 58 separated in the front-back direction.

In a cross section at a position provided with the intermediate portions 58 along the width direction W (a cross section illustrated in FIG. 3), the top sheet 50 is provided with the first projections 511, the first depressions 521, and the first projections 511 in this order. These portions are provided adjacent to each other in the width direction. In the first depression 521, the first depressed bottom portions 531, the first groove portion 541, the first depressed bottom portions 531, the intermediate portions 58, the first depressed bottom portions 531, the first groove portion 541, and the first depressed bottom portions 531 are provided adjacent to each other in this order. In the cross section along the width direction W taken at the position between the intermediate portions 58 in the front-back direction, the top sheet 50 is provided with the first projections 511, the first depressions 521, and the first projection 511 in this order adjacent to each other in the width direction, and the first depressions 521 is provided with the first depressed bottom portions 531, the first groove portions 541, and the first depressed bottom portions 531 in this order adjacent to each other in the width direction.

With the intermediate portions 58 provided between the first projections 511 in the width direction, when the first projections 511 are deformed in a falling direction, the first projections 511 are caught by the intermediate portions 58, and thus the first depressions 521 are prevented from being covered entirely and completely by the first projections 511 adjacent in the width direction. The top portions of the intermediate portions 58 are located on the non-skin-facing side T2 with respect to the top portions of the first projections 511 and the height of the intermediate portions 58 is low. Therefore, when the intermediate portions 58 and the first projections 511 are deformed in a falling direction, the first depressions 521 can hardly be covered with the intermediate portions 58 and the first projections 511. Therefore, when feces are discharged, the feces can be maintained in a state of being easily introduced into the first depressions.

The density of the fibers of the first groove wall portions 551 is lower than the density of the fibers of the first groove bottom portions 561. Since the density of the fibers of the first groove wall portions 551 is relatively low, moisture contained in excrement such as feces stored in the first depressions 521 may be introduced into the absorber 40 via voids between fibers. In addition, since the density of the fibers in the first groove bottom portions 561 is relatively high, the first groove bottom portions 561 can be continuously in contact with feces stored in the first depressions 521, and thus the feces can easily be retained by being surrounded by the first groove wall portions 551 and the first groove bottom portions 561. Therefore, the feces stored in the first depressions 521 can hardly be flowed out of the first depressions and is prevented from re-attaching to the wearer.

The portion having a high fiber density and a portion having a low fiber density may be determined in the following method. The fiber density may be determined by magnifying target portions of the sheet (for example, a portion of 1 mm×1 mm in size) by a microscope such as a digital microscope or an electronic microscope to a size on the order of approximately 100 times and comparing the number of fibers present in the sheet surfaces within an unit surface area. Preferably, confirmation is performed on thirty points each in the first region, and target portions having a tendency to have a large number of fibers are determined to be regions having a high fiber density.

In the top sheet 50 of the second region R2, the second projections 512 and the second depressions 522 are formed. In the top sheet 50 of the second region R2, the widthwise projection and the intermediate portion are not formed. A plurality of rows of the second projections 512 are provided continuously in the front-back direction L at a predetermined interval in the width direction W. The plurality of rows of the second projections 512 are arranged in parallel with the adjacent second projections 512. The second depressions 522 are provided between the second projections 512 in the width direction W. The length of the second depressions 522 in the front-back direction is longer than the length of the first depressions 521 in the front-back direction. The second depressions 522 may be formed continuously in the front-back direction as in the present exemplary embodiment, or may not be continuous in the front-back direction. Since the length of the second depressions 522 in the front-back direction is longer than the length of the first depressions 521 in the front-back direction, urine discharged into the second region can easily be diffused in the front-back direction. Therefore, urine can be introduced into a large surface area in the second region, and thus the urine can be absorbed quickly.

The second depressions 522 each include a second depressed bottom portions 532 as the depressed bottom portion 53, the second groove portions 542 as the groove portions 54, the second groove wall portions 552 as the groove wall portions 55, and the second groove bottom portions 562 as the groove bottom portions 56. The density of the fibers of the second groove wall portions 552 is lower than the density of the fibers of the second groove bottom portions 562. Since the density of the fibers of the second groove wall portions 552 is relatively low, moisture of urine stored in the second depressions 522 may be introduced into the absorber 40 via voids between fibers.

Since the top sheet 50 is provided with a plurality of depressions and projections, spaces are formed between the top sheet 50 and the absorber 40. The spaces extend continuously in the front-back direction in the non-skin-facing side of the projections 51 of the top sheet 50 and extend continuously or non-continuously in the front-back direction on the non-skin-facing side of the depressions of the top sheet 50. In this manner, with the spaces formed between the top sheet 50 and the absorber 40, body fluids introduced through the top sheet 50 may be introduced into the spaces, and thus excrement can be absorbed quickly by the absorber and, consequently, the body fluids remaining on the top sheet may be reduced.

The height (the length from the first groove bottom portions 561 to the top portions of the first projections 511) R1H of the top sheet in the first region R1 is larger than the height (the length from the second groove bottom portions 562 to the second projections 512) R2H of the top sheet in the second region R2. With the height of the top sheet in the first region R1 being relatively high, a distance between the wearer's skin and the absorber may be increased in a region where the first region is provided, and thus returning of a body fluids absorbed by the absorber to the skin side is prevented or reduced and the wearer's skin may be maintained in a dry state. In addition, the height of the first projections 511 (the length from the first depressed bottom portions 531 to the top portions of the first projections 511) 511H is larger than the height of the second projections 512 (the length from the second depressed bottom portions 532 to the second projections 512) 512H. Feces discharged onto the first region R1 are stored in the first depressions 521 between the first projections 511. At this time, since the height 511H of the first projections 511 is higher than the height 512H of the second projections 512, relatively high walls may be formed by the first projections 511. Since the walls that hold feces are high, feces stored once in the first depressions 521 may easily retained by the first projections 511. Consequently, even when the wearer's skin touches the surface of feces stored in the first depressions 521, the feces is continuously retained in the first depressions 521 and is prevented from exiting the first depressions 521 and re-attaching to the wearer.

Since the height 512H of the second projections 512 is smaller than the height 511H of the first projections 511, texture of the second region R2 may be improved. The crotch region 25 touches an egestion port of the wearer. The crotch region 25 is in tight contact with the wearer's skin compared with the rear waistline region 30. Since the height 512H of the second projections 512 in the second region R2, which corresponds to the crotch region 25, is reduced, contact of the second projections 512 with the skin may be alleviated even when the crotch region located in the second region R2 is in tight contact with the skin. The texture is improved, and thus wear feeling of the wearers is improved. In view of improvement of wear feeling as described above, the surface area of the second region R2 may be larger than the surface area of the first region R1. By providing the second region R2 having a desirable textile with a large surface area, wear feeling may be improved.

The first projections 511 and the second projections 512 are continued in the front-back direction L. In other words, the projections 51 extend across the first region R1 and the second region R2. In this configuration, body fluids such as urine are introduced in the front-back direction along the projections and are diffused across the first region R1 and the second region R2. Accordingly, the body fluids such as urine may be absorbed further quickly.

The first depressions 512 and the second depressions 522 are continued in the front-back direction L. In the first region R1 and the second region R2, the space in each of the first depressions 521 and the space in each of the second depressions 522 communicate with each other. In this configuration, excrement may be diffused smoothly between the first region and the second region. For example, even when the wearing position of the absorbent article is shifted and thus feces are discharged in the second region, the feces may be introduced into the first region, and stored and absorbed by the first region.

The erectile portions 83 of the three-dimensional gathers 80 extend across the first region R1 and the second region R2. Since the projections 51 are disposed across the first region R1 and the second region R2, generation of difference in rigidity due to the discontinuity of the projection in the area where the erectile portion 83 rises is difficult. Bending points due to the difference in rigidity can hardly be formed and thus maintenance of erecting properties of the three-dimensional gather is easily achieved. Leakage prevention walls formed by the three-dimensional gathers 80 are provided outer sides in the width direction of feces stored in the first depressions 521, and thus attachment of feces to portions around the wearer's legs may be prevented.

The intermediate portions 58 of the first region R1 continues to the second projections 512 in the front-back direction L. The intermediate portions 58 and the second projections 512 have the same shape and the same height in cross-section along the width direction. The intermediate portions 58 are portions not subjected to a second shaping process in the manufacturing process of the top sheet 50 described later, and are portions formed as second projections in the first shaping process and maintained in shape of the second projections. By a continuous configuration of the intermediate portions 58 and the second projections 512 as well, an effect of diffusion of urine in the front-back direction and an effect of enhancing erecting property of the three-dimensional gather may also be achieved.

An angle α formed between the first projecting wall portion 591 and the first depressed bottom portion 531 adjacent to the first projecting wall portion 591 (see FIG. 3) in the first region R1 is larger than an angle ß formed between a second projecting wall portion 592 and the second depressed bottom portion 532 adjacent to the second projecting wall portion 592 (see FIG. 4) in the second region R2. The rising angle α of the first projecting wall portion 591 is larger than the rising angle ß of the second projecting wall portion 592, and the first projecting wall portion 591 has a relatively steep inclination. Therefore, excrement stored in the first depressions 521 by the first projections 511 is easily retained, and the excrement once stored is prevented from exiting the first depressions 521.

The rising angle α of the second projecting wall portion 592 is smaller than the rising angle ß of the first projecting wall portion 591, and the second projecting wall portion 592 has a relatively gentle inclination. The second region R2 is disposed at least in the crotch region 25. The crotch region 25 is in tight contact with the wearer's skin compared with the rear waistline region 30. Since the projecting wall portions of the second region R2 have a gentle inclination, contact of the second projections 512 with the skin may be alleviated even when the crotch region located in the second region R2 is in tight contact with the skin.

Note that the rising angle of the projecting wall portions is measured in the following method. Using a cold spray or the like, a sheet to be measured is taken out from the absorbent article, and a projection and the periphery of the projection at a position to be measured are cut in parallel to the width direction. Cutting is to be performed with a sharp cutting blade (for example, a replacement blade of a cutter) so as to keep the projection from collapsing. The top sheet is placed on a horizontal plane paying attention that the cut sheet is not wrinkled, and a cut surface is magnified 20 times by a microscope and is photographed. A rising angle of skin-facing side surface (a surface after removal of shaggy fibers) of the projecting wall portions of the photographed cut surface with respect to the horizontal surface is measured.

The fibers in the first projecting wall portion 591 and the fibers in the second projecting wall portion 592 include more fibers oriented along the direction of thickness of the top sheet than fibers oriented in the front-back direction and the width direction. According to the absorbent article configured as described above, since spaces are formed on the non-skin-facing side of the projections, contact of the projections with respect to the skin becomes soft and thus the wearer can have a fluff feeling. The fibers of the projecting wall portions include many fibers oriented in the thickness direction, and thus body fluids tend to be introduced in the thickness direction. Therefore, even when the height of the projections is high, body fluids in the projecting wall portions may be introduced quickly toward the absorber, and thus remaining of the body fluids in the projecting wall portions are prevented or reduced.

Note that "the orientation of fibers in the projection walls are oriented in the thickness direction" means that the fibers are oriented within a range of +45 degrees to −45 degrees with respect to the thickness direction (from the skin facing side to the non-skin facing side of the sheet) in a state in which the projections and depressions are formed in the sheet. Measurement of the orientation of the fibers was performed by using a digital microscope VHX-100 manufactured by KEYENCE CORPORATION according to the following measuring method (1) Set a sample on an observation table so as to allow observation of a surface of a projecting wall portion, (2) Focus a lens on a nearest fiber of the sample except for fibers irregularly protruding toward the near side, (3) Prepare a three-dimensional (3D) image on a Personal Computer (PC) Display. Subsequently, (4) Convert the 3D image to a two-dimensional (2D) image, (5) Draw a plurality of parallel lines which divide the thickness direction of the projecting wall portion equally as needed within a measurement range. (6) Count the number of fibers oriented in respective directions in each of cells segmentalized by drawing the parallel lines, and (7) Calculate a ratio of the number of fibers oriented in the thickness direction with respect to the total number of fibers in a preset range and a ratio of the number of fibers oriented in a direction orthogonal to the thickness direction to achieve measurement and calculation.

The second depressions 522 are continuously arranged from a front end edge of the first region R1 to a front end edge of the top sheet 50. Since the second depressions 522 are formed continuously, body fluids may be smoothly diffused from the front end edge of the first region R1 to the front end edge of the top sheet to quickly transfer urine to the absorber in a large surface area.

A pitch 511P of the first projections 511 in the width direction is longer than the pitch 512P of the second projections 512 in the width direction. The pitch of the projections 51 in the width direction corresponds to a distance between widthwise centers of the respective projections adjacent in the width direction. Since the pitch 511P of the first projections 511 in the width direction is longer than the pitch 512P of the second projections 512 in the width direction, spaces between the first projections 511 become wider and thus spaces for storing feces may be widely formed. Therefore, feces discharged on the top sheet 50 are stored in the first depressions 521 and thus can hardly remain on the first projections 511. Contact of feces with the wearer's skin is prevented or reduced, and thus wear feeling is improved. In addition, more feces can be retained in the depressions of the first region, and thus the own weight of feces in the depressions is increased. With the increase in own weight of feces, the top sheet having fibers allows moisture contained in the feces to pass through gaps between the fibers into the absorber. Therefore, the moisture in the feces is transferred quickly into the absorber, and thus loose feces containing much moisture is prevented or reduced from being continuously in kept in contact with the skin.

The pitch 511P of the first projections 511 in the width direction may be longer than 2 mm and not longer than 5 mm. The pitch 512P of the second projections 512 in the width direction may be not smaller than 0.5 mm and not longer than 2 mm. In this configuration, the second region that mainly absorbs urine may have a smooth texture, while the first region that mainly absorbs feces may have thick and safety texture that ensures absorption. By providing portions having different textures in one top sheet of the disposable diaper, the wearer may have a perception of a feature gentle to the skin and capability to securely absorb feces.

Figure 7A:
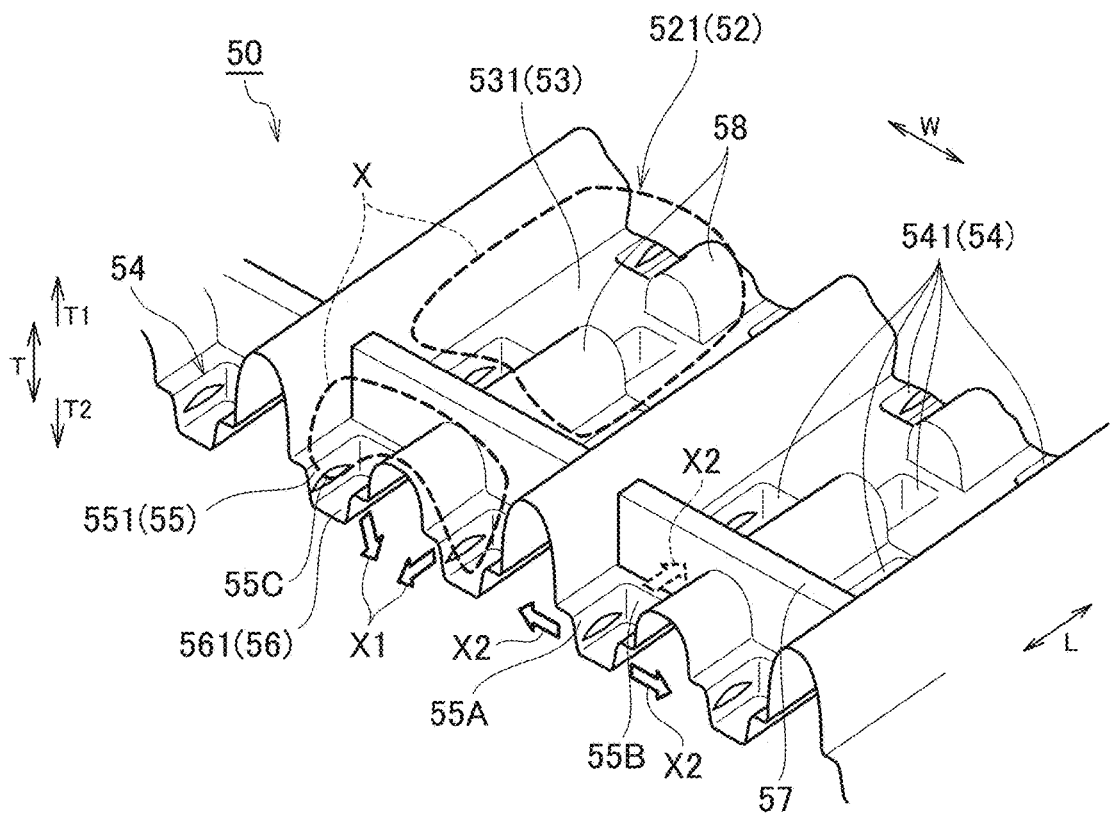
FIGS. 7A and 7B are drawings schematically illustrating a moving state of excrement when the excrement is discharged on the top sheet.
Figure 7B:
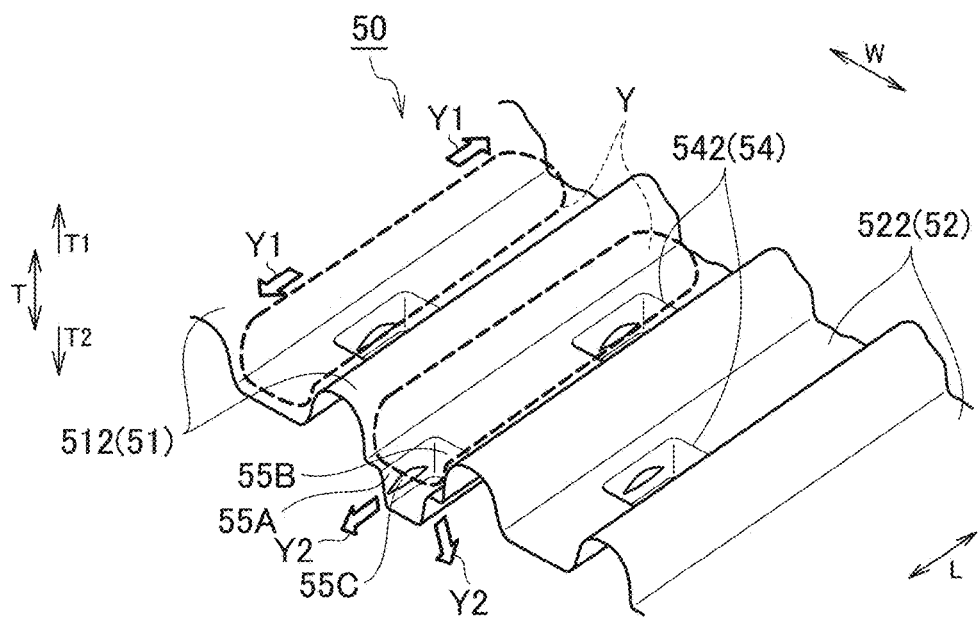

FIGS. 7A and 7B are schematic drawings illustrating a state of movement of excrement when the excrement is discharged on the top sheet. FIG. 7A illustrates a state of movement in the first region R1, and FIG. 7B illustrates a state of movement in the second region R2. When feces X is discharged onto the first region R1, feces X is stored in the first depressions 521 between the first projections 511. The feces X is held by the first projections 511 from both sides, and stays in the first depressions 521. Since the first depression is divided in the front-back direction by the widthwise projection, the feces stored in the first depressions is not diffused easily in the front-back direction. Loose feces containing much moisture is transfers to the absorber located on the non-skin-facing side of the top sheet via holes 55C formed in the first groove wall portions 551 of the first depressions 521 and the first depressed bottom portions 531 (arrow X1 in FIG. 7A). Body fluids such as moisture contained in feces and urine transfer to the absorber via the holes 55C, and also transfer to the absorber through the top sheet via the first groove wall portions 551 having a relatively low fiber density (Arrows X2 in FIG. 7A).

In contrast, when urine Y is discharged onto the second region R2, the urine Y is diffused in the front-back direction L via the second depressions 522 between the second projections 512 (Arrows Y1 in FIG. 7B). The urine is introduced into the second groove portions 542 disposed intermittently in the front-back direction, passes through the top sheet via the second groove wall portions 552 and the holes 55C, and transfers to the absorber (Arrows Y2 in FIG. 7B). In this manner, while urine is diffused in the second region R2, is transferred quickly to the absorber, loose feces and body fluids are transferred to the absorber and solid feces is retained in the first region R1. Accordingly, body fluids and loose feces are prevented from being attached to the wearer's skin and improvement of wear feeling is achieved. With the first region R1 and the second region R2 of the top sheet, urine and feces having different features can be absorbed adequately.

A front end edge R1F of the first region R1 is located rearward of a center of the disposable diaper 10 in the front-back direction L, and is located rearward of the first low basis-weight portions 41 of the absorbing core 40a. When wearing, in the disposable diaper 10, a bending point connecting a pair of the first low basis-weight portions 41 located in the front part and a bending point connecting a pair of the first low basis-weight portions 41 located in the rear part are formed. A portion between the two bending points is placed facing the crotch of the wearer. The first region R1 is located rearward of the first low basis-weight portions 41 and is disposed so as to come into contact with the buttocks. Therefore, feces can be stored smoothly in the depressions in the first region R1.

The rear end edge R1R of the first region R1 is located forward of the second low-basis-weight portion 42 of the absorbing core 40a. The second low-basis-weight portion 42 is provided at a rear end edge of the absorbing core 40a. At the time of wearing, the absorbing cores located on the outer sides of the second low-basis-weight portion 42 in the width direction are deformed toward each other by contraction of the waist elastic portion 85, and a rear end edge of the absorbing core 40a forms a cup shape that covers the buttocks of the wearer. Since the rear end edge of the absorbing core 40a rises toward the wearer, feces is prevented from flowing rearward of the rear end edge of the absorbing core 40a. In addition, since the first region R1 is disposed on the crotch side with respect to the second low-basis-weight portion 42, feces is reliably trapped in the first region to promote retention and absorption of the excrement in the first region, and leakage of feces from the back is prevented. The first region R1 is located forward of the second low-basis-weight portion 42. Therefore, even when the absorbing core 40a is deformed starting from the second low-basis-weight portion 42, relatively flat state is maintained. Therefore, a state of introducing feces easily into the depressions in the first region may be maintained.

Four corners of the first region R1 in plan view have a curved shape. The shape of the wearer's body is generally such that the buttocks side where the rear waistline region 30 is disposed swells up more than the ventral side where the front waistline region 20 is disposed. Since the four corners of the first region R1 has a curved shape, the four corners of the first region R1 easily conform with the body when the rear waistline region 30 is disposed on the wearer along the round portions of the buttocks, and thus improved wear feeling is achieved. The first projections located at four corners of the first region continue to the second projections in the front-back direction. Therefore, the four corners of the first region R1 easily conform with the body when the rear waistline region 30 is disposed on the wearer along the round portions of the buttocks, and thus improved wear feeling is achieved.

The rear end edge R1R of the first region R1 is located rearward of the contracting region S1 of the erectile portion 83. The second fixed portion 82 side of the erectile portion 83 is closer to the rising point, and thus the rising height can hardly be created compared with the center of the erectile portion 83 in the front-back direction. Also, a region rearward of the contracting region S1 is not contracted by the side resilient member 71, and thus the rising height of the erectile portion 83 can hardly be created. Since the first region R1 is disposed rearward of the contracting region S1, rigidity of the top sheet 50 on the second fixed portion 82 side in the rear waistline region 30 is increased. By the increased rigidity of the top sheet 50 located on the non-skin-facing side T2 of the erectile portion 83, the erectile portion 83 can erect easily and the height of the erectile portion 83 can be created further easily. Therefore, sideward leakage of feces in the rear waistline region 30 may be prevented. Since the erectile portions 83 can easily rise, the top sheet 50 cannot be covered easily with the three-dimensional gathers 80, and thus discharged feces can easily be introduced into the first depressions 521.

The rear end edge R1R of the first region R1 is located forward of a region between a pair of fastening portions 91. The region between the pair of fastening portions 91 is a region connecting the left and right fastening portions 91 of the fastening tapes 90. The first region R1 is at a distance from the area between the pair of fastening portions 91. The region between the pair of fastening portions 91 is an area where the fastening portions 91 come into tight contact with the body in a state of being fastened to the front waistline region 20. Since the region between the pair of fastening portions 91 and the first region R1 are apart from each other, a state in which feces stored in the depressions in the first region R1 is separated from the wearer's skin is easily achieved.

The rear end edge of the first region R1 is located forward of the waist elastic portion 85. The first region R1 is at a distance from the region where the waist elastic portion 85 is disposed. The region where the waist elastic portion 85 is disposed is a region coming into tight contact with the body in a worn state. Since the first region R1 and the region where the waist elastic portion 85 is disposed are at the distance from each other, a state in which feces stored in the depressions in the first region R1 is separated from the wearer's skin is easily achieved.

The first region R1 is disposed between the pair of first fixed portions 81 in the width direction. An outer edge of the first region R1 is located inside the first fixed portions 81 in the width direction. Rigidity of the top sheet 50 between the first fixed portions 81 in the rear waistline region 30 is enhanced and thus the height of the erectile portions may be easily created. Therefore, sideward leakage of feces in the rear waistline region may be prevented. Since the erectile portions 83 can easily rise, the top sheet cannot be covered easily with the three-dimensional gathers 80, and thus discharged feces can easily be introduced into the depressions.

(3) A Top Sheet Manufacturing Apparatus and a Method of Manufacturing the Same

Figure 8:
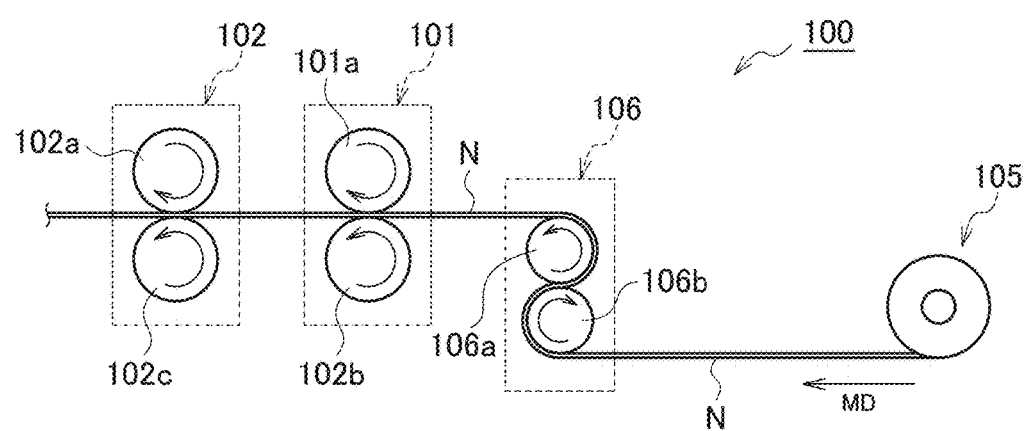
FIG. 8 is a drawing schematically illustrating an example of a manufacturing apparatus for manufacturing the top sheet.

An apparatus and a manufacturing method for manufacturing a non-woven fabric constituting the top sheet will be described with reference to FIG. 8 to FIG. 14. FIG. 8 is a drawing schematically illustrating an example of a manufacturing apparatus 100 for manufacturing a non-woven fabric which constitutes the top sheet. The manufacturing apparatus 100 includes an unwinding device 105 having a non-woven fabric N to be processed wound thereon in a roll state and configured to unwind a non-woven fabric N in a carrying direction MD, a preheating device 106 configured to preheat the non-woven fabric N supplied from the unwinding device 105, and a shaping device configured to stretch the preheated non-woven fabric N to form projections and depressions (including groove portions). The shaping device includes a first shaping device 101 and a second shaping device 102. When the method of manufacturing the non-woven fabric N by using the manufacturing apparatus 100, a preheating step for preheating the non-woven fabric N unwound from the unwinding device 105, a first shaping step for stretching and applying a shaping process to the non-woven fabric N after having been subjected to the preheating step, and a second shaping step for stretching and shaping the non-woven fabric N after having been subjected to the first shaping process are performed in sequence.

The preheating device 106 is disposed downstream of the unwinding device 105 in the carrying direction, and preheats the non-woven fabric N supplied from the unwinding device 105. The preheating device 106 includes a pair of upper and lower heating rolls 106a and 106b and is capable of winding the non-woven fabric N that is carried thereto on the rotating lower heating roll 106b and heating the non-woven fabric N thereon, sending the non-woven fabric N to the rotating upper heating roll 106a, and re-heating the non-woven fabric N by the heating roll 106a. In the preheating step, the non-woven fabric N unwound from the unwinding device 105 and carried along the carrying direction MD is brought into contact with outer peripheral surfaces of the heating rolls 106a and 106b of the preheating device 106 in sequence to perform preheating by heating the non-woven fabric N.

Figure 9:
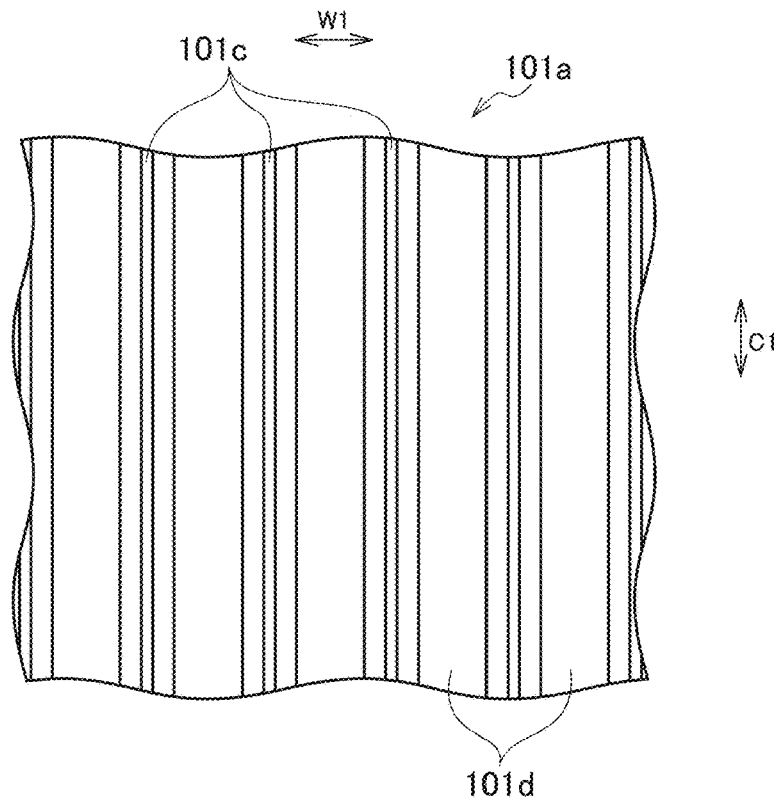
FIG. 9 is a plan view schematically illustrating an outer peripheral surface of a first disk roll of a first shaping device.
Figure 10:
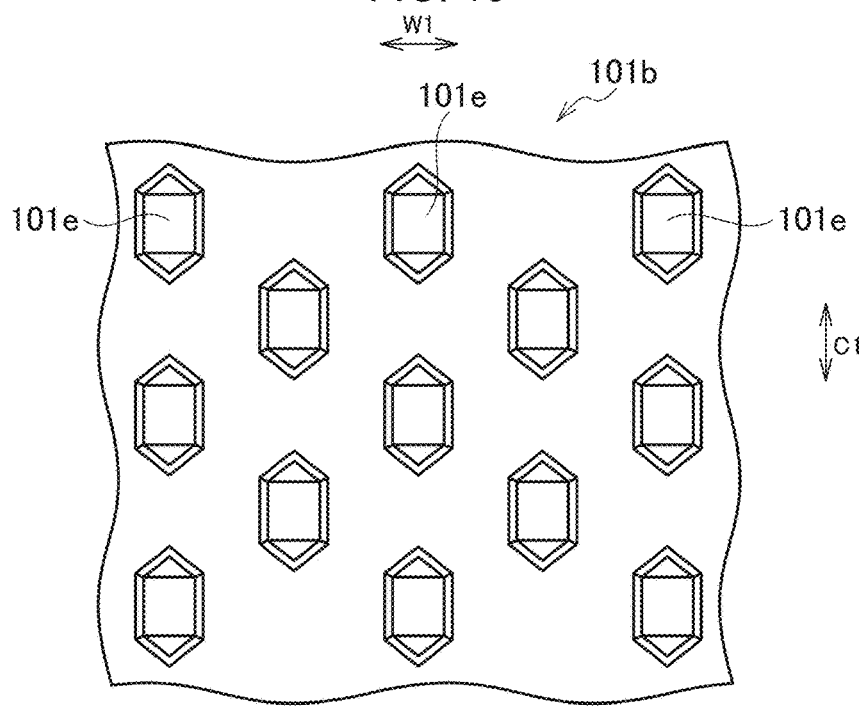
FIG. 10 is a plan view schematically illustrating an outer peripheral surface of a first pin roll of the first shaping device.
Figure 11:
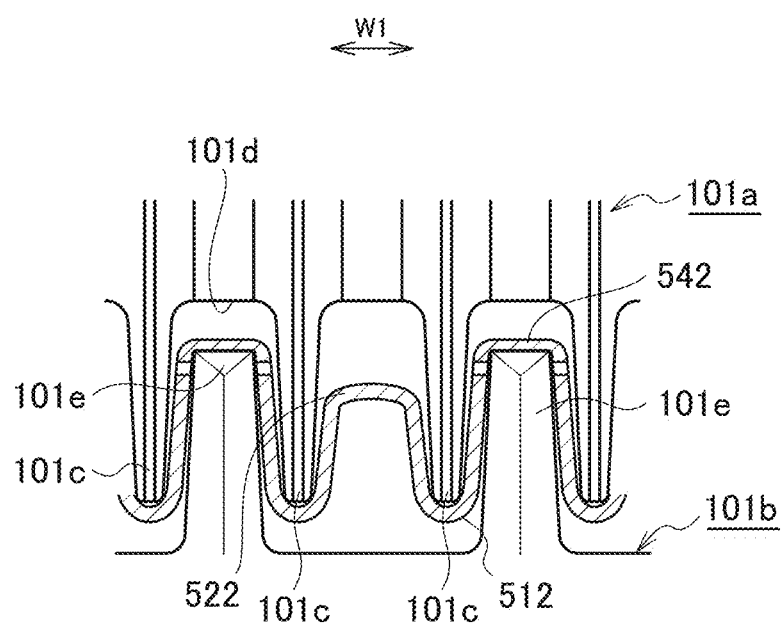
FIG. 11 is a principal enlarged view illustrating an engaged state between a first disk roll and a first pin roll of the first shaping device.

The first shaping device 101 is disposed downstream of the carrying direction MD of the preheating device 106. The first shaping device 101 forms the second projections 512 and the second depressions 522 in a region corresponding to the entire range of the top sheet 50 in the width direction. The first shaping device 101 includes an upper first disk roll 101a and a lower first pin roll 101b. FIG. 9 is a plan view schematically illustrating an outer peripheral surface of the first disk roll 101a, and FIG. 10 is a plan view schematically illustrating an outer peripheral surface of the first pin roll 101b. FIG. 11 is a principal enlarged view illustrating an engaged state between the first disk roll and the first pin roll of the first shaping device.

The first disk roll 101a includes projecting ridges 101c disposed at regular intervals in the roll width direction W1, and a plurality of rows of depressed grooves 101d provided between adjacent projecting ridges 101c. The projecting ridges 101c and the depressed grooves 101d are provided alternately in the roll width direction W1, and are provided continuously in a roll circumferential direction C1. In contrast, the first pin roll 101b includes a plurality of pins 101e provided to engage the depressed grooves 101d of the first disk roll 101a on an outer peripheral surface thereof. As illustrated in FIG. 11, these pins 101e are disposed at regular intervals to avoid contact with the projecting ridges 101c of the first disk roll 101a in the roll width direction W1, and are disposed substantially linearly at regular intervals along the outer peripheral surface in the roll circumferential direction C1. As illustrated in FIG. 9, the plurality of pins 101e are disposed in a staggered manner on an outer peripheral surface of the first pin roll 101b.

In the first shaping step, the non-woven fabric N carried after the preheating step is passed between the pair of upper and lower rolls 101a and 101b in the first shaping device 101 and the non-woven fabric is stretched and shaped between the projecting ridges 101c and the depressed grooves 101d of the first disk roll 101a and the pins 101e of the first pin roll 101b. At this time, the first disk roll 101a pushes a part in contact between the projecting ridges 101c and the non-woven fabric N in the direction of the first pin roll 101b, and thus the second projections 512 are shaped.

The first pin roll 101b pushes part of the non-woven fabric N in contact with the plurality of pins 101e arranged in a row in the circumferential direction with the pins 101e into the same depressed grooves 101d of the first disk roll 101a. At this time, portions of the non-woven fabric N pulled into the depressed grooves 101d in a state of non-contact with the pins 101e are formed into the second depressions 522. Parts of the non-woven fabric in contact with distal end portions of the pins 101e are pushed strongly into the depressed grooves 101d and thus are shaped. Portions in contact with the distal end portions of the pins 101e are formed into the second groove portions 542. In each of the second groove portions 542, first groove surfaces 55A extending in the direction of extension of the second projection 512 and the second depression 522, second groove surfaces 55B extending in the roll width direction, and the second groove bottom portion 562 are formed. The second groove bottom portions 562 at the time of formation substantially have a higher fiber density than other portion because the distal end portions of the pins 101e pushes the abutting portions of the non-woven fabric N into the depressed grooves 101d in a state in which the first disk roll 101a and the first pin roll 101b engage the non-woven fabric N.

At parts of the non-woven fabric N in contact with both end portions of the distal end portions of the pins 101e in the width direction (roll width direction), the pins 101e may push through thermoplastic resin fibers that form the first groove surfaces 55A or may break the fibers with the aid of tension generating when the projecting ridges 101c pushes the non-woven fabric N in the direction of the first pin roll 101b. Accordingly, the holes 55C are formed in the second groove portions 542. Here, the holes 55C are formed in the first groove surfaces 55A along the carrying direction MD of the non-woven fabric N, that is, along the direction of extension of the second projections 512 and the second depressions 522.

Figure 12:
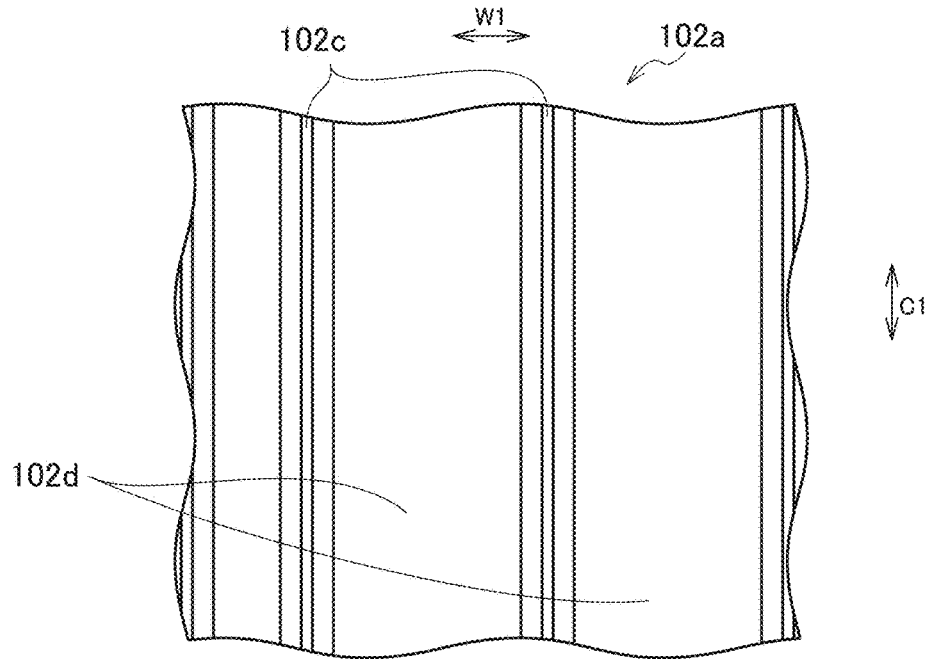
FIG. 12 is a plan view schematically illustrating an outer peripheral surface of a second disk roll of a second shaping device.
Figure 13:
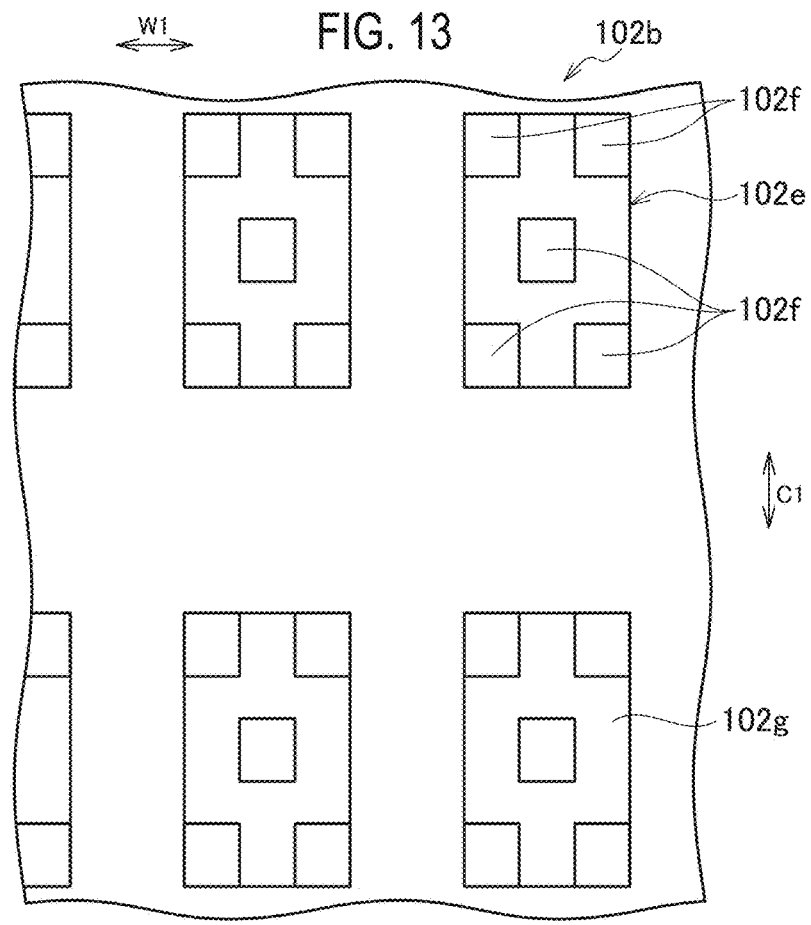
FIG. 13 is a plan view schematically illustrating an outer peripheral surface of a second pin roll of the second shaping device.
Figure 14:
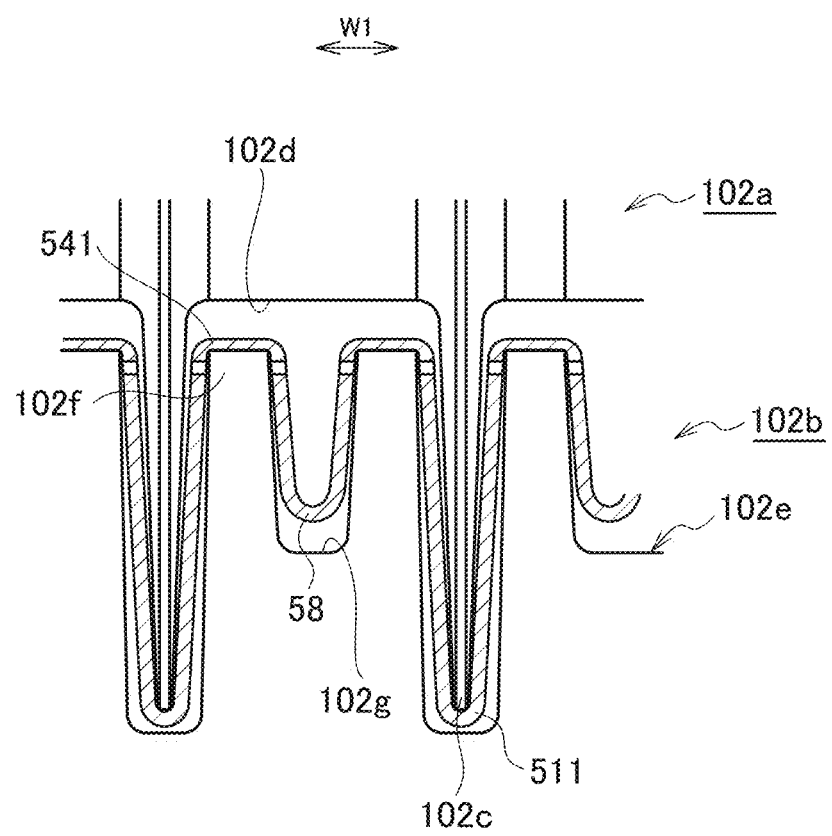
FIG. 14 is a principal enlarged view illustrating an engaged state between the second disk roll and the second pin roll of the second shaping device.

The second shaping device 102 is disposed downstream of the first shaping device 101 in the carrying direction. The second shaping device 102 forms the first projections 511, the first depressions 521, the intermediate portions 58, and the widthwise projections 57 in a region corresponding to the first region R1. The second shaping device 102 includes an upper second disk roll 102a and a lower second pin roll 102b. FIG. 12 is a plan view schematically illustrating an outer peripheral surface of the second disk roll 102a, and FIG. 13 is a plan vie schematically illustrating an outer peripheral surface of the second pin roll 102b. FIG. 14 is a principal enlarged view illustrating an engaged state between the second disk roll and the second pin roll of the second shaping device.

The second disk roll 102a includes projecting ridges 102c disposed at regular intervals in the roll width direction W1, and a plurality of rows of depressed grooves 102d provided between the adjacent projecting ridges 102c. The projecting ridges 102c and the depressed grooves 102d are provided alternately in the roll width direction W1, and are provided continuously in the roll circumferential direction C1. In contrast, the second pin roll 102b includes a plurality of pins 102e provided on an outer peripheral surface to engage the depressed grooves 102d of the second disk roll 102a. The pins 102e are not provided over the entire outer peripheral surface of the second pin roll 102b, and are provided only on a region corresponding to the first region R1. The second shaping device 102 performs the shaping process only on a region corresponding to the first region R1, and does not perform the shaping process on other regions. Therefore, only the shaping process by the first shaping device 101 is performed on other regions.

As illustrated in FIG. 14, the pins 102e of the second pin roll are disposed to avoid contact with the projecting ridges 102c of the second disk roll 102a in the roll width direction, and are disposed substantially linearly at regular intervals along the roll width direction. The pins 102e are disposed substantially linearly at regular intervals along the outer peripheral surface in the roll circumferential direction C1. The pins 102e are rectangular in plan view. The pins 102e are each provided with projecting portions 102f and the recessed portion 102g. The projecting portions 102f project toward the second disk roll and are provided in regions corresponding to the first groove portions 541. The recessed portions 102g recess toward the outer peripheral surface with respect to the projecting portions 102f, and are provided in regions corresponding to the intermediate portions 58 and the first depressed bottom portions 531.

In the second shaping step, the non-woven fabric N carried after the first shaping step is passed through the second shaping device 102 between the pair of upper and lower rolls 102a and 102b and the non-woven fabric is stretched and shaped between the projecting ridges 102c and the depressed grooves 102d, which engage with each other, of the second disk roll 102a and the pins 102e of the second pin roll 102b. At this time, the second disk roll 102a pushes a portion of contact between the projecting ridges 102c and the non-woven fabric N in the direction of the second pin roll 102b, and thus the first projections 511 are shaped.

The height of the projecting ridges 102c of the second disk roll 102a is higher than the height of the projecting ridges 101c of the first disk roll. Therefore, the height 511H of the first projections 511 is larger than the height 512H of the second projections 512. The pitch of the projecting ridges 102c of the second disk roll 102a in the roll width direction W1 is longer than the pitch of the projecting ridges 101c of the first disk roll 101a in the roll width direction W1. More specifically, the pitch of the projecting ridges 102c of the second disk roll 102a in the roll width direction W1 is twice the pitch of the projecting ridges 101c of the first disk roll 101a in the roll width direction. Therefore, one second projection 512 of the adjacent second projections in the width direction is shaped by the first projection 511. The other second projection 512 is maintained in the state of the second projection 512 and constitutes the intermediate portion 58 in the first region R1, or is shaped by the first groove portion 541.

The recessed portions 102g or the projecting portions 102f are located at the centers between the projecting ridges 102c in the roll width direction W1. In a cross section passing the centers of the pins 102e in the roll width direction W1 and taken along the roll circumferential direction C1, the projecting portions 102f are located at the centers of the pins 102e in the roll circumferential direction C1, and the recessed portions 102g are disposed on both outer sides of the projecting portions 102f in the roll circumferential direction C1. The second projections 512 are formed by the first shaping device at the center between the projecting ridges 102c in the roll width direction (the center of the pins 102e in the roll width direction). The recessed portions 102g located at the centers between the projecting ridges 102c in the roll width direction do not shape the non-woven fabric. Therefore, parts corresponding to the recessed portions 102g located at the centers between the projecting ridges 102c are maintained in the state of the second projections 512. Parts maintained in the state of the second projections 512 constitute the intermediate portions 58 in the first region R1. In contrast, the projecting portions 102f located at the centers between the projecting ridges 102c shape the first groove portions 541.

The second pin roll 102b pushes part of the non-woven fabric N in contact with the plurality of pins 102e arranged in a row in the roll circumferential direction C1 and the roll width direction W1 with the pins 102e into the same depressed grooves 102d of the second disk roll 102a. At this time, parts of the non-woven fabric N pulled into the depressed grooves 102d in a state of non-contact with the pins 102e are provided at a distance in the roll circumference direction and are formed into the widthwise projections 57. Parts in contact with the projecting portions 102f located at four corners of the pins 102e in plan view are pushed strongly into the depressed grooves 102d and thus are shaped. Parts in contact with the projecting portions 102f of the pins 102e shape the first groove portion 541. First groove surfaces 55A extending in the direction of extension of the first projections 511 and the first depressions 521, and second groove surfaces 55B extending in the roll width direction, and the first groove bottom portions 561 are formed in each of the first groove portions 541. The first groove bottom portions 561 at the time of formation substantially have a higher fiber density than other portion because the distal end portions of the pins 102e push the abutting portions of the non-woven fabric N into the depressed grooves 102d in a state in which the second disk roll 102a and the second pin roll 102b engage the non-woven fabric N. The pins 102e may push through thermoplastic resin fibers that form the first groove surfaces 55A or may break the fibers with the aid of tension generating when the projecting portions 102fc push the non-woven fabric N. Accordingly, the holes 55C are formed in the second groove portions 542. Here, the holes 55C are formed in the first groove surfaces 55A along the carrying direction MD of the non-woven fabric N, that is, in the direction of rotation of the rolls 102a and 102b along the direction of extension of the second projections 512 and the second depressions 522.

Parts in contact with the recessed portions (recessed portions located outside the respective pins in the roll width direction) between the projecting portions at the four corners in the roll circumference direction is shaped into the first depressed bottom portions 531. Also, parts in contact with the depressed portions of the projecting portions at four corners in the roll width direction (the recessed portions located outside the respective pins in the roll circumference direction) are not shaped and remains in the state of the second projections and constitute the intermediate portions. With the manufacturing apparatus and the manufacturing method as described thus far, the top sheet 50 according to the present exemplary embodiment may be manufactured.

As described above, the contents of the present invention has been disclosed throughout the exemplary embodiment of the present invention, and the statement and the drawings which constitute part of this disclosure should not be understood to limit the present invention. Various alternative embodiments, examples, and operations will be apparent for those skilled in the art from this disclosure. Therefore, the technical scope of the present invention is defined only by specific matters of the invention according to claims adequate from the description given above.

The three-dimensional gather is not limited to the configuration described in the exemplary embodiment described above. The erectile portion of the three-dimensional gather according to the embodiment described above is configured to rise inward in the width direction. The erectile portion of the three-dimensional gather according to a modification may be configured to rise outward in the width direction. The three-dimensional gather according to the modification may be formed by folding out the side sheets 70 in the width direction and fixing ends of the folded portion in the front-back direction, and fixing the end portion of the folded portion in the front-back direction to the side sheet or the like. In the three-dimensional gather according to the modification, the end portion of the folded portion in the front-back direction is located outside the contracting region in the front-back direction and constitutes the second fixed portion.

The entire contents of Japanese Patent Application No. 2016-96718 filed in May 13, 2016 are incorporated herein by reference.

INDUSTRIAL APPLICABILITY

An absorbent article capable of absorbing urine and feces exhibiting different behaviors adequately by absorbing urine quickly and retaining the feces once stored continuously may be provided.

The invention claimed is:

1. An absorbent article, comprising:
a front waistline region;
a rear waistline region;
a crotch region located between the front waistline region and the rear waistline region;
a front-back direction from the front waistline region toward the rear waistline region;
a width direction orthogonal to the front-back direction;
an absorber extending across the crotch region and extending to at least one of the front waistline region and the rear waistline region; and
a top sheet located on a skin-facing side with respect to the absorber and coming into contact with a wearer,
the top sheet including projections projecting toward a skin-facing side and depressions provided between the projections,
the projections and the depressions extending in the front-back direction and being arranged alternately in the width direction,
wherein the top sheet includes a first region disposed at least in the rear waistline region and a second region disposed at least in the crotch region,
a height of the projections in the first region is larger than a height of the projections in the second region,
each of the depressions in the first region includes a dividing portion configured to divide a space in each of the depressions, the space extending in the front-back direction,
a pitch of the projections in the first region in the width direction is larger than a pitch of the projections in the second region in the width direction,
each of the projections includes a projecting wall portion extending from an outer edge of the projection toward the skin-facing side,
each of the depressions includes a depressed bottom portion extending in the front-back direction and the width direction, and
an angle formed between the projecting wall portion and the depressed bottom portion of the depression adjacent to the projecting wall portion in the first region is larger than an angle formed between the projecting wall portion and the depressed bottom portion of the depression adjacent to the projecting wall portion in the second region.

2. An absorbent article, comprising:
a front waistline region;
a rear waistline region;
a crotch region located between the front waistline region and the rear waistline region;
a front-back direction from the front waistline region toward the rear waistline region;
a width direction orthogonal to the front-back direction;
an absorber extending across the crotch region and extending to at least one of the front waistline region and the rear waistline region; and
a top sheet located on a skin-facing side with respect to the absorber and coming into contact with a wearer,
the top sheet including projections projecting toward a skin-facing side and depressions provided between the projections,
the projections and the depressions extending in the front-back direction and being arranged alternately in the width direction,
wherein the top sheet includes a first region disposed at least in the rear waistline region and a second region disposed at least in the crotch region,
a height of the projections in the first region is larger than a height of the projections in the second region,
each of the depressions in the first region includes a dividing portion configured to divide a space in each of the depressions, the space extending in the front-back direction,
a pitch of the projections in the first region in the width direction is larger than a pitch of the projections in the second region in the width direction,
each of the depressions in the first region includes a depressed bottom portion extending in the front-back direction and the width direction and an intermediate portion projecting toward the skin-facing side with respect to the depressed bottom portion, and a top portion of the intermediate portion is located on a non-skin-facing side of top portions of the projections in the first region.

3. An absorbent article, comprising:
a front waistline region;
a rear waistline region;
a crotch region located between the front waistline region and the rear waistline region;
a front-back direction from the front waistline region toward the rear waistline region;
a width direction orthogonal to the front-back direction;
an absorber extending across the crotch region and extending to at least one of the front waistline region and the rear waistline region; and
a top sheet located on a skin-facing side with respect to the absorber and coming into contact with a wearer,
the top sheet including projections projecting toward a skin-facing side and depressions provided between the projections,
the projections and the depressions extending in the front-back direction and being arranged alternately in the width direction,
wherein the top sheet includes a first region disposed at least in the rear waistline region and a second region disposed at least in the crotch region,
a height of the projections in the first region is larger than a height of the projections in the second region,
each of the depressions in the first region includes a dividing portion configured to divide a space in each of the depressions, the space extending in the front-back direction,
a pitch of the projections in the first region in the width direction is larger than a pitch of the projections in the second region in the width direction,
wherein the absorbent article comprises a pair of three-dimensional gathers disposed on both of the outer sides in the width direction of the widthwise center of the absorbent article, and
each of the three-dimensional gathers includes:
an erectile portion including a resilient member elastic in the front-back direction and configured to be capable of erecting toward the wearer,
a first fixed portion located outside the erectile portion in the width direction and serving as a starting point of an erecting movement of the erectile portion, and a second fixed portion located at both outer sides of the erectile portion in the front-back direction and serving as a starting point of an erecting motion of the erectile portion, the first region is disposed between a pair of the first fixed portions in the width direction, and a rear end edge of the first region is located rearward of a region of the erectile portion contracted by the resilient member.

4. An absorbent article, comprising:

a front waistline region;

a rear waistline region;

a crotch region located between the front waistline region and the rear waistline region;

a front-back direction from the front waistline region toward the rear waistline region;

a width direction orthogonal to the front-back direction;

an absorber extending across the crotch region and extending to at least one of the front waistline region and the rear waistline region; and a top sheet located on a skin-facing side with respect to the absorber and coming into contact with a wearer, the top sheet including projections projecting toward a skin-facing side and depressions provided between the projections, the projections and the depressions extending in the front-back direction and being arranged alternately in the width direction, wherein the top sheet includes a first region disposed at least in the rear waistline region and a second region disposed at least in the crotch region, a height of the projections in the first region is larger than a height of the projections in the second region, each of the depressions in the first region includes a dividing portion configured to divide a space in each of the depressions, the space extending in the front-back direction, a pitch of the projections in the first region in the width direction is larger than a pitch of the projections in the second region in the width direction, the dividing portion projects toward the skin-facing side with respect to the depressed bottom portion, the depressed bottom portion extending in each of the depressions in the first region in the front-back direction and the width direction, and the dividing portion is disposed along the width direction between the projections in the first region, and the top portions of the projections in the first region is located on the skin-facing side with respect to a top portion of the dividing portion.

5. The absorbent article according to claim 1, wherein the depressions in the second region are disposed continuously from a front end edge of the first region to a front end edge of the top sheet.

6. The absorbent article according to claim 1, wherein each of the projections includes a projecting wall portion extending from an outer edge of the projection toward the skin-facing side, the top sheet includes fibers, a space is formed between the projections and the absorber, and the fibers in the projecting wall portion include fibers oriented along a thickness direction of the top sheet more than fibers oriented along the front-back direction and the width direction.

7. The absorbent article according to claim 1, further comprising a pair of three-dimensional gathers disposed on both outer sides in the width direction of a widthwise center of the absorbent article, wherein each of the three-dimensional gathers includes an erectile portion including a resilient member elastic in the front-back direction and capable of erecting toward the wearer, and the projections and the erectile portion are disposed across the first region and the second region.

8. The absorbent article according to claim 1, wherein the top sheet includes fibers, each of the depressions includes a depressed bottom portion extending in the front-back direction and the width direction and a groove portion depressed toward the non-skin-facing side with respect to the depressed bottom portion, the groove portion includes a groove wall portion extending from the depressed bottom portion toward the non-skin-facing side and a groove bottom portion located on the non-skin-facing side with respect to the groove wall portion, and a density of the fibers of the groove wall portion in the first region is lower than a density of fibers in the groove bottom portion.

9. The absorbent article according to claim 1, further comprising a pair of three-dimensional gathers disposed on both of the outer sides in the width direction of the widthwise center of the absorbent article, wherein each of the three-dimensional gathers includes:

the erectile portion including a resilient member elastic in the front-back direction and configured to be capable of erecting toward the wearer, and a first fixed portion located outside the erectile portion in the width direction and serving as a starting point of an erecting movement of the erectile portion, and the first region is disposed between a pair of the first fixed portions in the width direction.

10. The absorbent article according to claim 1, further comprising a pair of fastening tapes in the rear waistline region, the pair of fastening tapes extending outward in the width direction, wherein each of the fastening tapes includes a fastening portion to be fastened to the front waistline region, and the first region is at a distance from a region between the pair of fastening portions.

11. The absorbent article according to claim 1, further comprising a waist elastic portion disposed in the rear waistline region and elastic in the width direction, wherein the first region is at a distance from an area where the waist elastic portion is disposed.

* * * * *